US008718738B2

(12) United States Patent
Blank et al.

(10) Patent No.: US 8,718,738 B2
(45) Date of Patent: May 6, 2014

(54) METHOD AND APPARATUS FOR COUPLING A SAMPLE PROBE WITH A SAMPLE SITE

(75) Inventors: Thomas B. Blank, Gilbert, AZ (US); Roxanne E. Abul-Haj, Mesa, AZ (US)

(73) Assignee: GLT Acquisition Corp., Irvine, CA (US)

( * ) Notice: Subject to any disclaimer, the term of this patent is extended or adjusted under 35 U.S.C. 154(b) by 1248 days.

(21) Appl. No.: 12/393,867

(22) Filed: Feb. 26, 2009

(65) Prior Publication Data
US 2009/0247840 A1 Oct. 1, 2009

Related U.S. Application Data

(63) Continuation-in-part of application No. 11/031,103, filed on Jan. 6, 2005, now abandoned, which is a continuation-in-part of application No. 11/335,773, filed on Jan. 18, 2006, now abandoned, application No. 12/393,867, which is a continuation of application No. 10/472,856, filed on Sep. 18, 2003, now Pat. No. 7,133,710, and application No. 10/472,856, filed as application No. PCT/US03/07065 on Mar. 7, 2003.

(60) Provisional application No. 60/536,197, filed on Jan. 12, 2004, provisional application No. 60/534,834, filed on Jan. 6, 2004, provisional application No. 60/566,568, filed on Apr. 28, 2004, provisional application No. 61/032,859, filed on Feb. 29, 2008, provisional application No. 60/362,885, filed on Mar. 8, 2002.

(51) Int. Cl.
*A61B 5/00* (2006.01)
*G02B 6/24* (2006.01)

(52) U.S. Cl.
USPC .............. 600/344; 385/39; 600/316; 600/322

(58) Field of Classification Search
USPC ............................... 600/310–344; 385/15–52
See application file for complete search history.

(56) References Cited

U.S. PATENT DOCUMENTS 4,033,054 A 7/1977 Fukuoka
4,213,462 A 7/1980 Sato
(Continued)

FOREIGN PATENT DOCUMENTS

CN 1214768 4/1999
DE 2640987 3/1978
(Continued)

OTHER PUBLICATIONS

Webster's II New Riverside University Dictionary: The Riverside Publishing Company, 1994, p. 1000.
(Continued)

*Primary Examiner* — Max Hindenburg
*Assistant Examiner* — John Pani
(74) *Attorney, Agent, or Firm* — Knobbe, Martens, Olson & Bear LLP

(57) ABSTRACT

The invention comprises method and apparatus for fluid delivery between a sample probe and a sample. The fluid delivery system includes: a fluid reservoir, a delivery channel, a manifold or plenum, a channel or moat, a groove, and/or a dendritic pathway to deliver a thin and distributed layer of a fluid to a sample probe head and/or to a sample site. The fluid delivery system reduces sampling errors due to mechanical tissue distortion, specular reflectance, probe placement, and/or mechanically induced sample site stress/strain associated with optical sampling of the sample.

28 Claims, 12 Drawing Sheets

(56) References Cited

U.S. PATENT DOCUMENTS

| | | | |
|---|---|---|---|
| 4,272,040 A | 6/1981 | Bastian et al. |
| 4,291,293 A | 9/1981 | Yamada et al. |
| 4,321,930 A | 3/1982 | Jobsis |
| 4,548,505 A | 10/1985 | Ono |
| 4,674,338 A | 6/1987 | Carpenter |
| 4,685,464 A | 8/1987 | Goldberger et al. |
| 4,732,450 A * | 3/1988 | Lee ................................. 385/33 |
| 4,755,413 A | 7/1988 | Morris |
| 4,798,955 A | 1/1989 | Rosenthal |
| 4,830,014 A | 5/1989 | Goodman et al. |
| 4,866,644 A | 9/1989 | Shenk et al. |
| 4,882,492 A | 11/1989 | Schlager |
| 5,007,423 A | 4/1991 | Branstetter et al. |
| 5,039,492 A | 8/1991 | Saaski et al. |
| 5,068,536 A | 11/1991 | Rosenthal |
| 5,070,874 A | 12/1991 | Barnes et al. |
| 5,131,391 A | 7/1992 | Sakai et al. |
| 5,170,786 A | 12/1992 | Thomas |
| 5,285,783 A | 2/1994 | Secker |
| 5,299,570 A | 4/1994 | Hatschek |
| 5,348,003 A | 9/1994 | Caro |
| 5,361,758 A | 11/1994 | Hall et al. |
| 5,398,681 A | 3/1995 | Kupershmidt |
| 5,448,662 A | 9/1995 | Kittell |
| 5,492,118 A | 2/1996 | Gratton |
| 5,506,482 A | 4/1996 | Teramatsu |
| 5,507,288 A | 4/1996 | Bocker et al. |
| 5,517,301 A | 5/1996 | Dave |
| 5,548,674 A | 8/1996 | Rondeau |
| 5,574,855 A | 11/1996 | Rosich et al. |
| 5,596,987 A | 1/1997 | Chance |
| 5,619,195 A | 4/1997 | Allen |
| 5,632,273 A | 5/1997 | Suzuki |
| 5,636,634 A | 6/1997 | Kordis |
| 5,655,530 A | 8/1997 | Messerschmidt |
| 5,661,843 A | 8/1997 | Rickenbach |
| 5,671,317 A | 9/1997 | Weishaupt |
| 5,687,717 A | 11/1997 | Halpern et al. |
| 5,725,480 A | 3/1998 | Ooste |
| 5,730,140 A | 3/1998 | Fitch |
| 5,747,806 A | 5/1998 | Khalil et al. |
| 5,750,994 A | 5/1998 | Schlager |
| 5,769,076 A | 6/1998 | Maekawa |
| 5,770,454 A | 6/1998 | Essenpreis et al. |
| 5,772,347 A | 6/1998 | Gueret |
| 5,823,951 A | 10/1998 | Messerschmidt |
| 5,825,488 A | 10/1998 | Kohl et al. |
| 5,830,132 A | 11/1998 | Robinson |
| 5,869,075 A | 2/1999 | Krzysik |
| 5,877,664 A | 3/1999 | Jackson, Jr. |
| 5,879,373 A | 3/1999 | Roper et al. |
| 5,891,021 A | 4/1999 | Dillon |
| 5,912,656 A | 6/1999 | Tham et al. |
| 5,935,062 A | 8/1999 | Messerschmidt et al. |
| 5,945,676 A | 8/1999 | Khalil et al. |
| 5,956,150 A | 9/1999 | Kanne |
| 5,978,691 A | 11/1999 | Mills |
| 6,014,756 A | 1/2000 | Dottling |
| 6,040,578 A | 3/2000 | Malin et al. |
| 6,045,511 A | 4/2000 | Ott |
| 6,067,463 A | 5/2000 | Jeng et al. |
| 6,088,605 A | 7/2000 | Griffith et al. |
| 6,093,156 A | 7/2000 | Cunningham et al. |
| 6,095,974 A | 8/2000 | Shemwell et al. |
| 6,115,673 A | 9/2000 | Malin et al. |
| 6,119,031 A | 9/2000 | Crowley |
| 6,144,868 A | 11/2000 | Parker |
| 6,147,749 A | 11/2000 | Kubo et al. |
| 6,152,876 A | 11/2000 | Robinson |
| 6,157,041 A | 12/2000 | Thomas et al. |
| 6,167,290 A | 12/2000 | Yang et al. |
| 6,178,564 B1 | 1/2001 | Leonard et al. |
| 6,180,416 B1 | 1/2001 | Kuenik et al. |
| 6,230,034 B1 | 5/2001 | Messerschmidt |
| 6,233,471 B1 | 5/2001 | Berner et al. |
| 6,236,047 B1 | 5/2001 | Malin et al. |
| 6,240,306 B1 | 5/2001 | Rohrscheib et al. |
| 6,253,097 B1 | 6/2001 | Aronow et al. |
| 6,272,364 B1 | 8/2001 | Kurnik |
| 6,280,381 B1 | 8/2001 | Malin et al. |
| 6,289,230 B1 | 9/2001 | Chaiken et al. |
| 6,304,766 B1 | 10/2001 | Colvin, Jr. |
| 6,326,160 B1 | 12/2001 | Dunn et al. |
| 6,330,464 B1 | 12/2001 | Colvin, Jr. et al. |
| 6,334,360 B1 | 1/2002 | Chen |
| 6,381,489 B1 | 4/2002 | Ashibe |
| 6,400,974 B1 | 6/2002 | Lesho |
| 6,405,065 B1 | 6/2002 | Malin et al. |
| 6,411,373 B1 | 6/2002 | Garside et al. |
| 6,411,838 B1 | 6/2002 | Nordstrom et al. |
| 6,415,167 B1 | 7/2002 | Blank et al. |
| 6,421,549 B1 | 7/2002 | Jacques |
| 6,441,388 B1 | 8/2002 | Thomas |
| 6,442,408 B1 | 8/2002 | Wenzel et al. |
| 6,449,500 B1 | 9/2002 | Asai et al. |
| 6,456,870 B1 | 9/2002 | Rennert et al. |
| 6,475,800 B1 | 11/2002 | Hazen et al. |
| 6,487,429 B2 | 11/2002 | Hockersmith et al. |
| 6,493,566 B1 | 12/2002 | Ruchti et al. |
| 6,501,982 B1 | 12/2002 | Ruchti et al. |
| 6,507,687 B1 | 1/2003 | Juskaitis et al. |
| 6,512,937 B2 | 1/2003 | Blank et al. |
| 6,512,982 B2 | 1/2003 | Yang et al. |
| 6,526,300 B1 | 2/2003 | Kiani et al. |
| 6,528,809 B1 | 3/2003 | Thomas |
| 6,546,269 B1 | 4/2003 | Kurnik |
| 6,558,320 B1 | 5/2003 | Causey et al. |
| 6,574,490 B2 | 6/2003 | Abbink et al. |
| 6,585,370 B2 | 7/2003 | Zelman |
| 6,631,282 B2 | 10/2003 | Rule et al. |
| 6,641,533 B2 | 11/2003 | Causey, III et al. |
| 6,690,958 B1 | 2/2004 | Walker et al. |
| 6,788,965 B2 | 9/2004 | Ruchti |
| 6,839,583 B1 | 1/2005 | Lewandowski et al. |
| 6,920,345 B2 | 7/2005 | Al-Ali et al. |
| 6,927,843 B2 | 8/2005 | Dick |
| 7,133,710 B2 | 11/2006 | Acosta et al. |
| 7,178,063 B1 | 2/2007 | Smith |
| 7,409,330 B2 | 8/2008 | Kumamoto |
| 2002/0026106 A1 | 2/2002 | Khalil et al. |
| 2002/0058864 A1 | 5/2002 | Mansfield |
| 2002/0087949 A1 | 7/2002 | Golender et al. |
| 2003/0040663 A1 | 2/2003 | Rule |
| 2003/0156270 A1 | 8/2003 | Hunter |
| 2003/0208113 A1 | 11/2003 | Mault et al. |
| 2003/0216627 A1 | 11/2003 | Lorenz |
| 2003/0216630 A1 | 11/2003 | Jersey-Willuhn et al. |
| 2004/0068163 A1 | 4/2004 | Ruchti |
| 2004/0077937 A1 | 4/2004 | Yarden |
| 2004/0127777 A1 | 7/2004 | Ruchti |
| 2004/0163032 A1 | 8/2004 | Guo |
| 2004/0167473 A1 | 8/2004 | Moenning |
| 2004/0267105 A1 * | 12/2004 | Monfre et al. ................. 600/344 |
| 2005/0007125 A1 | 1/2005 | Heger |
| 2005/0034102 A1 | 2/2005 | Peck |
| 2005/0054908 A1 | 3/2005 | Blank et al. |
| 2005/0187439 A1 * | 8/2005 | Blank et al. .................... 600/310 |
| 2005/0267342 A1 | 12/2005 | Blank et al. |
| 2006/0200017 A1 | 9/2006 | Monfre et al. |
| 2006/0211931 A1 | 9/2006 | Blank et al. |
| 2006/0217602 A1 | 9/2006 | Abul-haj et al. |
| 2008/0009835 A1 | 1/2008 | Kriesel et al. |
| 2008/0033275 A1 | 2/2008 | Blank et al. |
| 2008/0319382 A1 | 12/2008 | Blank et al. |
| 2009/0062635 A1 | 3/2009 | Brauker et al. |
| 2009/0318786 A1 | 12/2009 | Blank et al. |

FOREIGN PATENT DOCUMENTS

| | | |
|---|---|---|
| EP | 1254631 | 11/2002 |
| JP | 04-215742 | 8/1992 |
| JP | 05-317295 | 12/1993 |
| JP | 08-215180 | 8/1996 |
| JP | 2001-037741 | 2/2001 |

(56) References Cited

FOREIGN PATENT DOCUMENTS

| | | |
|---|---|---|
| JP | 2001-299727 | 10/2001 |
| JP | 2002535023 | 10/2002 |
| WO | WO 96/28084 | 9/1996 |
| WO | WO 97/05819 | 2/1997 |
| WO | WO 97/28437 | 8/1997 |
| WO | WO 00/22982 | 4/2000 |
| WO | WO 00/42907 | 7/2000 |
| WO | WO 00/74562 | 12/2000 |
| WO | WO 00/76575 A3 | 12/2000 |
| WO | WO 01/31304 | 5/2001 |
| WO | WO 01/58355 | 8/2001 |
| WO | WO 01/72222 | 10/2001 |
| WO | WO 01/82794 | 11/2001 |
| WO | WO 02/065090 | 8/2002 |

OTHER PUBLICATIONS

Diabetes Statistics. Bethesda, MD: National Institute of Health, Publication No. 98/3926, Nov. 1997.

The Diabetes Control and Complications Trial Research Group. "The effect of intensive treatment of diabetes on the development and progression of long-term complications in insulin-dependent diabetes mellitus." N Eng J of Med 1993;329:977-86.

U.K. Prospective Diabetes Study (UKPDS) Group, "Intensive blood-glucose control with sulphonylureas or insulin compared with conventional treatment and risk of complications in patients with type 2 diabetes," *Lancet*, vol. 352, pp. 837-853, 1998.

Ohkubo, Y., H. Kishikawa, E. Araki, T. Miyata, S. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes mellitus: a randomized prospective 6-year study," *Diabetes Res Clin Pract*, vol. 28, pp. 103-117, 1995.

Savitzky, A. and M. J. E. Golay. "Smoothing and Differentiation of Data by Simplified Least Squares Procedures," Anal. Chem., vol. 36, No. 8, pp. 1627-1639, 1964.

Hazen, Kevin H. "Glucose Determination in Biological Matrices Using Near-Infrared Spectr Sage, Burton H. "FDA Panel Approves Cygnus's Noninvasive GlucoWatchÔ", *Diabetes Technology & Therapeutics*, 2, 2000, 115-116.oscopy", doctoral dissertation, University of Iowa, 1995.

Tamada, J.A., S. Garg, L. Jovanovic, K.R. Pitzer, S. Fermi, R.O. Potts, "Noninvasive Glucose Monitoring Comprehensive Clinical Results," *JAMA*, vol. 282, No. 19, pp. 1839-1844, Nov. 17, 1999.

"GlucoWatch Automatic Glucose Biographer and AutoSensors", Cygnus Inc., Document #1992-00, Rev. Mar. 2001.

Trajanoski, Zlatko; Brunner, Gernot A.; Schaupp, Lucas; Ellmerer, Martin; Wach, Paul; Pieber, Thomas R.; Kotanko, Peter; Skrabai, Falko "Open-Flow Microperfusion of Subcutaneous Adipose Tissue for ON-Line Continuous Ex Vivo Measurement of Glucose Concentration", *Diabetes Care*, 20, 1997, 1114-1120.

Trajanoski, Zlatko; Wach, Paul; Gfrerer, Robert "Portable Device for Continuous Fractionated Blood Sampling and Continuous ex vivo Blood Glucose Monitoring", *Biosensors and Bioelectronics*, 11, 1996, 479-487.

Gross, Todd M.; Bode, Bruce W.; Einhorn, Daniel; Kayne, David M.; Reed, John H.; White, Neil H.; Mastrototaro, John J. "Performance Evaluation of the MiniMed Continuous Glucose Monitoring System During Patient Home Use", *Diabetes Technology & Therapeutics*, 2, 2000, 49-56.

Rebrin, Kerstin; Steil, Gary M.; Antwerp, William P. Van; Mastrototaro, John J. "Subcutaneous Glucose Predicts Plasma Glucose Independent of Insulin: Implications for Continuous Monitoring", *Am., J. Physiol.*, 277, 1999, E561-E571, 0193-1849/99, The American Physiological Society, 1999.

Geladi, P., D. McDougall and H. Martens. "Linearization and Scatter-Correction for Near-Infrared Reflectance Spectra of Meat," Applied Spectroscopy, vol. 39, pp. 491-500, 1985.

R.J. Barnes, M.S. Dhanoa, and S. Lister, Standard Normal Variate Transformation and De-trending of Near-Infrared Diffuse Reflectance Spectra, *Applied Spectroscopy*, 43, pp. 772-777, 1989.

T. Isaksson and B. R. Kowalski, "Piece-Wise Multiplicative Scatter Correction Applied to Near-Infrared Diffuse Transmittance Data From Meat Products", *Applied Spectroscopy*, 47, pp. 702-709, 1993.

H. Martens and E. Stark, "Extended multiplicative signal correction and spectral interference subtraction: new preprocessing methods for near infrared spectroscopy", *J. Pharm Biomed Anal*, 9, pp. 625-635, 1991.

T. ITRsaksson, Z. Wang, and B. R. Kowalski, Optimised scaling (OS-2) regression applied to near infrared . . . food products, *J. Near Infrared Spectroscopy*, 1, pp. 85-97, 1993.

Sum, S.T., "Spectral Signal Correction for Multivariate Calibration," Doctoral Disseration, University of Delaware, Summer 1998.

Sum, S.T. and S.D. Brown, "Standardization of Fiber-Optic Probes for Near-Infrared Multivariate Calibrations," *Applied Spectroscopy*, vol. 52, No. 6, pp. 869-877, 1998.

T. B. Blank, S.T. Sum, S.D. Brown and S.L. Monfre, "Transfer of near-infrared multivariate calibrations without standards," *Analytical Chemistry*, 68, pp. 2987-2995, 1996.

Oppenheim, Alan V. and R. W. Schafer, *Digital Signal Processing*, Englewood Cliffs, NJ: Prentice Hall, 1975, pp. 195-271.

Otto, M., Statistics and Computer Application in Analytical Chemistry; *Chemometrics*, Weinheim: Wiley-VCH, 1999.

Beebe, K.R., R.J. Pell and M.B. Seasholtz, *Chemometrics A Practical Guide*, New York: John Wiley & Sons, Inc., 1998.

M.A. Sharaf, D.L. Illman and B.R. Kowalski, *Chemometrics*, New York: John Wiley & Sons, Inc., 1996.

Massart, et al.; *Data Handling in Science and Technology*—vol. 2; Chemometrics: a textbook; 1988 Elsevier Science. Publishing Co., Inc. pp. 215-253.

\* cited by examiner

METHOD AND APPARATUS FOR COUPLING A SAMPLE PROBE WITH A SAMPLE SITE

CROSS REFERENCE TO RELATED APPLICATION

This application:
is a continuation-in-part of U.S. patent application Ser. No. 11/031,103, filed Jan. 6, 2005, which claims priority from U.S. provisional patent application Ser. No. 60/536,197, filed Jan. 12, 2004; U.S. provisional patent application Ser. No. 60/534,834, filed Jan. 6, 2004; and U.S. provisional patent application Ser. No. 60/566,568, filed Apr. 28, 2004;
is a continuation-in-part of U.S. patent application Ser. No. 11/335,773, filed Jan. 18, 2006, which is a continuation of U.S. patent application Ser. No. 10/472,856, filed Sep. 18, 2003, which claims priority from PCT application no. PCT/US03/07065, filed Mar. 7, 2003, which claims benefit of U.S. provisional patent application Ser. No. 60/362,885, filed Mar. 8, 2002; and
claims benefit of U.S. provisional patent application No. 61/032,859, filed Feb. 29, 2008,
all of which are incorporated herein in their entirety by this reference thereto.

BACKGROUND OF THE INVENTION

1. Field of the Invention

This invention relates generally to the noninvasive measurement of biological parameters through near-infrared spectroscopy. More particularly, a method and apparatus are disclosed for fluid delivery between an analyzer and a tissue sample to aid in parameter stability during optical sampling.

2. Discussion of the Prior Art

Technical Background

In-vivo measurement of tissue properties or analyte concentration using optical based analyzers require that a tissue measurement region be positioned and coupled with respect to an optical interface or probe, such as a tip of a sampling module. The requirements of a sampling interface system for probe placement and coupling depends upon the nature of the tissue properties and analytes under consideration, the optical technology being applied, and the variability of the tissue sample site. Demanding in-vivo applications require a high degree of sampling reproducibility. In one example, a relatively unskilled operator or user must perform the optical measurement. One exemplary application is the noninvasive estimation of glucose concentration through near-infrared spectroscopy in a variety of environments. This problem is further considered through a discussion of the target application and the structure, variability, and dynamic properties of live tissue.

Diabetes

Diabetes is a chronic disease that results in abnormal production and use of insulin, a hormone that facilitates glucose uptake into cells. Diabetics have increased risk in three broad categories: cardiovascular heart disease, retinopathy, and neuropathy. The estimated total cost to the United States economy alone exceeds $90 billion per year. *Diabetes Statistics*, National Institutes of Health, Publication No. 98-3926, Bethesda, Md. (November 1997). Long-term clinical studies show that the onset of diabetes related complications are significantly reduced through proper control of blood glucose concentrations [The Diabetes Control and Complications Trial Research Group, *The effect of intensive treatment of diabetes on the development and progression of long-term complications in insulin-dependent diabetes mellitus*, N Eng J of Med 1993; 329:977-86. A vital element of diabetes management is the self-monitoring of blood glucose concentration by diabetics in the home environment. However, current monitoring techniques discourage regular use due to the inconvenient and painful nature of drawing blood through the skin prior to analysis.

Noninvasive Glucose Concentration Estimation

There exist a number of noninvasive approaches for glucose concentration estimation. These approaches vary widely, but have at least two common steps. First, an apparatus is used to acquire a reading from the body without obtaining a biological sample for every glucose concentration estimation. Second, an algorithm is used to convert the noninvasive reading into a glucose concentration estimation or determination.

Technologies

A number of previously reported technologies for estimating glucose concentration noninvasively exist that involve the measurement of a tissue related variable. One species of noninvasive glucose concentration analyzer uses spectroscopy to acquire a signal or spectrum from the body. Examples include far-infrared absorbance spectroscopy, tissue impedance, Raman, and fluorescence, as well as techniques using light from the ultraviolet through the infrared [ultraviolet (200 to 400 nm), visible (400 to 700 nm), near-infrared (700 to 2500 nm or 14,286 to 4000 $cm^{-1}$), and mid-infrared (2500 to 14,285 nm or 4000 to 700 $cm^{-1}$)]. Notably, noninvasive techniques do not have to be based upon spectroscopy. For example, a bioimpedence meter is a noninvasive device. In this document, any device that reads glucose concentration from the body without penetrating the skin or collecting a biological sample with each sample is referred to as a noninvasive glucose concentration analyzer. For the purposes of this document, X-rays and magnetic resonance imagers (MRI's) are not considered to be defined in the realm of noninvasive technologies. It is noted that noninvasive techniques are distinct from invasive techniques in that the sample analyzed is a portion of the human body in-situ, not a biological sample acquired from the human body. The actual tissue volume that is sampled is the portion of irradiated tissue from which light is diffusely reflected, transflected, or diffusely transmitted to the spectrometer detection system.

Instrumentation

A number of spectrometer configurations are reported for collecting noninvasive spectra of regions of the body. Typically a spectrometer has one or more beam paths from a source to a detector. Optional light sources include a blackbody source, a tungsten-halogen source, one or more light emitting diodes, or one or more laser diodes. For multi-wavelength spectrometers a wavelength selection device is optionally used or a series of optical filters are optionally used for wavelength selection. Wavelength selection devices include dispersive elements, such as one or more plane, concave, ruled, or holographic grating.

Sampling

Light is directed from a glucose concentration analyzer to a tissue sample site by optical methods, such as through a light pipe, fiber-optics, a lens system, free space optics, and/or a light directing mirror system. Typically, one or more of three modes are used to collect noninvasive scans: transmittance, transflectance, and/or diffuse reflectance. Collected signal is converted to a voltage and sampled through an analog-to-digital converter for analysis on a microprocessor based system and the result displayed.

Human Tissue/Light Interaction

When incident light is directed onto the skin surface, a part of it is reflected while the remaining part penetrates the skin surface. The proportion of reflected light energy is strongly dependent on the angle of incidence. At nearly perpendicular incidence, about four percent of the incident beam is reflected due to the change in refractive index between air ($\eta_D=1.0$) and dry stratum corneum ($\eta_D=1.55$). For normally incident radiation, this specular reflectance component is as high as seven percent, because the very rigid and irregular surface of the stratum corneum produces off-normal angles of incidence. Regardless of skin color, specular reflectance of a nearly perpendicular beam from normal skin ranges between four and seven percent over the entire spectrum from 250 to 3000 nm. The air-stratum corneum border gives rise to a regular reflection. Results indicate that the indices of refraction of most soft tissue (skin, liver, heart, etc) lie within the 1.38-1.41 range with the exception of adipose tissue, which has a refractive index of approximately 1.46. The 93 to 96 percent of the incident beam that enters the skin is attenuated due to absorption and/or scattering within any of the layers of the skin. These two processes taken together essentially determine the penetration of light into skin, as well as remittance of scattered light from the skin.

Noninvasive Glucose Concentration Determination

There are a number of reports of noninvasive glucose technologies. Some of these relate to general instrumentation configurations required for noninvasive glucose concentration estimation while others refer to sampling technologies. Those related to the present invention are briefly reviewed, infra.

Specular Reflectance

R. Messerschmidt, D. Sting, *Blocker device for eliminating specular reflectance from a diffuse reflectance spectrum*, U.S. Pat. No. 4,661,706 (Apr. 28, 1987) describe a reduction of specular reflectance by a mechanical device. A blade-like device "skims" the specular light before it impinges on the detector. This system leaves alignment concerns and improvement in efficiency of collecting diffusely reflected light is needed.

R. Messerschmidt, M. Robinson, *Diffuse reflectance monitoring apparatus, U.S. Pat. No.* 5,636,633 (Jun. 10, 1997) describe a specular control device for diffuse reflectance spectroscopy using a group of reflecting and open sections.

R. Messerschmidt, M. Robinson, Diffuse reflectance monitoring apparatus, U.S. Pat. No. 5,935,062 (Aug. 10, 1999) and R. Messerschmidt, M. Robinson, Diffuse reflectance monitoring apparatus, U.S. Pat. No. 6,230,034 (May 8, 2001) describe a diffuse reflectance control device that discriminates between diffusely reflected light that is reflected from selected depths. This control device additionally acts as a blocker to prevent specularly reflected light from reaching the detector.

S. Malin, G Khalil, Method and apparatus for multi-spectral analysis of organic blood analytes in noninvasive infrared spectroscopy, U.S. Pat. No. 6,040,578 (Mar. 21, 2000) describe the use of specularly-reflected light in regions of high water absorbance, such as 1450 and 1900 nm, to mark the presence of outlier spectra wherein the specularly reflected light is not sufficiently reduced.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe a mechanical device for applying sufficient and reproducible contact of the apparatus to the sample medium to minimize specular reflectance. Further, the apparatus allows for reproducible applied pressure to the sample site and reproducible temperature at the sample site.

Coupling Fluid

A number of sources describe coupling fluids as a consideration in noninvasive sampling methods and apparatus. Coupling fluids have been long known and understood in the field of optics. Some coupling fluids are used to fill optical irregularities. Others are used for refractive index matching. Some, such as glycerol when used in conjunction with near-infrared light, absorb in the wavelength region of interest. Several reports of optical coupling fluids and a report of a coupling fluid are described, infra.

R. Messerschmidt, Method for non-Invasive blood analyte measurement with improved optical interface, U.S. Pat. No. 5,655,530, Aug. 12, 1997 and R. Messerschmidt, Method for non-invasive blood analyte measurement with improved optical interface, U.S. Pat. No. 5,823,951, (Oct. 20, 1998) describe an index-matching medium to improve the interface between a sensor probe and a skin surface during spectrographic analysis. These patents teach an optical coupling medium containing both perfluorocarbons and chlorofluorocarbons that have minimal absorbance in the near-infrared. Since they are known carcinogens, chlorofluorocarbons (CFC's) are unsuitable for use in preparations to be used on living tissue. Furthermore, use of CFC's poses a well-known environmental risk. Additionally, Messerschmidt's interface medium is formulated with substances that are likely to leave artifacts in spectroscopic measurements.

M. Robinson, R. Messerschmidt, Method for non-invasive blood analyte measurement with improved optical interface, U.S. Pat. No. 6,152,876 (Nov. 28, 2000) and M. Rohrscheib, C. Gardner, M. Robinson, Method and apparatus for non-invasive blood analyte measurement with fluid compartment equilibration, U.S. Pat. No. 6,240,306 (May 29, 2001) describe an index-matching optical coupling fluid used to improve the interface between the sensor probe and skin surface during spectroscopic analysis. The index-matching medium is preferably a composition containing chlorofluorocarbons in combination with optionally added perfluorocarbons.

T. Blank, G. Acosta, M. Mattu, S. Monfre, Fiber optic probe guide placement guide, U.S. Pat. No. 6,415,167 (Jul. 2, 2002) describe a coupling fluid of one or more fluorocarbons where a quantity of the coupling fluid is placed at an interface of the tip of an optical probe of a sample module and a measurement site. Advantageously, perfluoro compounds and fluorocarbons lack the toxicity associated with chlorofluorocarbons.

Pressure

E. Chan, B. Sorg, D. Protsenko, M. O'Neil, M. Motamedi, A. Welch, *Effects of compression on soft tissue optical properties*, IEEE Journal of Selected Topics in Quantum Electronics, Vol. 2, no. 4, 943-950 (1996) describe the effect of pressure on absorption and reduced scattering coefficients from 400 to 1800 nm. Most specimens show an increase in the scattering coefficient with compression.

K. Hazen, G. Acosta, A. Abul-Haj, R. Abul-Haj, Apparatus and method for reproducibly modifying localized absorption and scattering coefficients at a tissue measurement site during optical sampling, U.S. Pat. No. 6,534,012 (Mar. 18, 2003) describe in a first embodiment a noninvasive glucose concentration estimation apparatus for either varying the pressure applied to a sample site or maintaining a constant pressure on a sample site in a controlled and reproducible manner by moving a sample probe along the z-axis perpendicular to the sample site surface. In an additional described embodiment, the arm sample site platform is moved along the z-axis that is perpendicular to the plane defined by the sample surface by raising or lowering the sample holder platform relative to the analyzer probe tip. The '012 patent further teaches proper contact between the probe tip and the sample site to be that point at which specularly-reflected light is substantially zero at the water bands at 1950 and 2500 nm.

M. Makarewicz, M. Mattu, T. Blank, G. Acosta, E. Handy, W. Hay, T. Stippick, B. Richie, Method and apparatus for minimizing spectral interference due to within and between sample variations during in-situ spectral sampling of tissue, U.S. patent application Ser. No. 09/954,856 (filed Sep. 17, 2001) describe a temperature and pressure controlled sample interface. The means of pressure control is a set of supports for the sample that control the natural position of the sample probe relative to the sample.

Data Processing

Several approaches exist that use diverse preprocessing and post processing methods to remove spectral variation related to the sample and instrument variation: These include: normalization, smoothing, derivatives, multiplicative signal correction, piecewise multiplicative scatter correction, extended multiplicative signal correction, pathlength correction with chemical modeling and optimized scaling, and finite impulse response filtering. A goal of these techniques is to attenuate the noise and instrument variation while maximizing the signal of interest.

Problem

It is desirable to provide a means of assuring that the same tissue sample volume is repeatably sampled, thus minimizing sampling errors due to mechanical tissue distortion, specular reflectance, and probe placement. It would also be highly advantageous to provide a coupling medium to provide a constant interface between an optical probe and the skin at a tissue measurement site. Still further, it would be advantageous to provide complete and uniform coverage of a sample site with the coupling fluid in an automated fashion.

SUMMARY OF THE INVENTION

The invention comprises a fluid delivery method and apparatus between a sample probe and a sample.

DETAILED DESCRIPTION OF THE INVENTION

The invention comprises a fluid delivery method and apparatus between a sample probe and a sample.

In one embodiment, a fluid delivery system includes use of: a fluid reservoir, a delivery channel, a manifold or plenum, a channel or moat, a groove, and/or a dendritic pathway to deliver a fluid to a sample probe head and/or a sample. For example, the fluid delivery system is used to place the fluid in a uniform manner substantially or completely covering a sample site, thus minimizing sampling errors due to mechanical tissue distortion, specular reflectance, probe placement, and/or mechanically induced sample site stress/strain is concurrent or subsequent optical sampling of the sample.

For example, a fluid or coupling fluid is delivered to a sample using the fluid delivery system. The fluid placed on the surface of tissue at a tissue measurement site, such as a coupling medium or alternatively an optical coupling fluid, is used to enhance performance of an optical analyzer coupled to the tissue measurement site. The system is optionally automated.

Sampling is controlled to enhance analyte concentration estimation derived from noninvasive sampling. More particularly, sampling is enhanced using controlled fluid delivery to a region between a tip of a sample probe and a tissue measurement site. The controlled fluid delivery enhances coverage of a skin sample site with the thin layer of fluid. Means for controlling the fluid delivery, coverage, and thickness are described, infra.

Herein, examples of coupling of a sample probe tip of a noninvasive glucose concentration analyzer to a skin sample site are used. However, the invention is generally used in coupling of an optical sampling device to a sampled medium, such as skin.

Analyzer

Figure 1A:
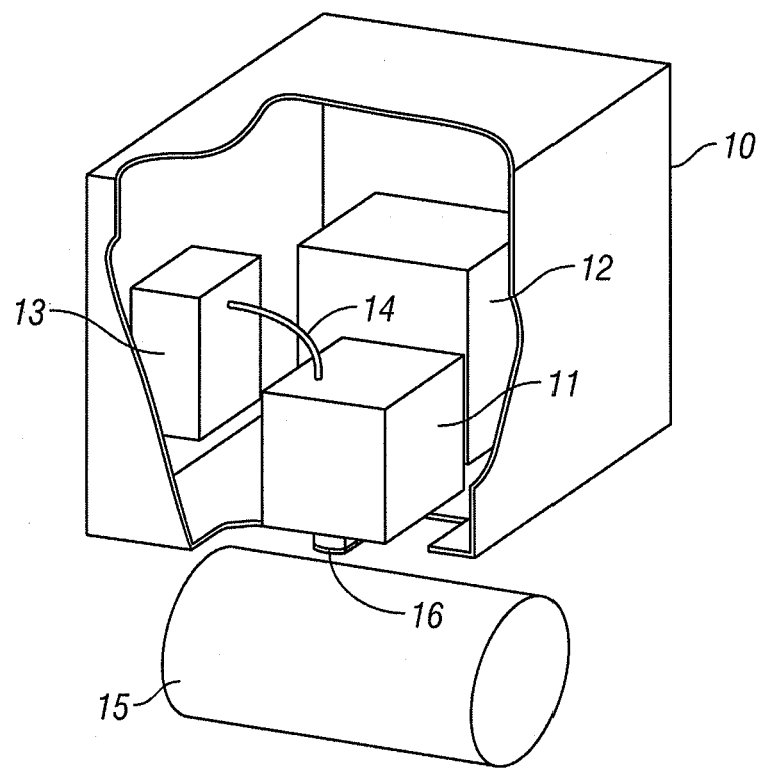
FIGS. 1A and 1B illustrate an analyzer comprising a sample module, a base module, and a fluid delivery module.

Referring now to FIG. 1A, an illustrative representation of a spectroscopic analyzer 10 is presented. Components of the analyzer 10 preferably include: a sample module 11, a detection module 12, and a coupling fluid delivery module 13. The sample module 11 preferably includes: a source, at least one light delivery optic, a coupling fluid delivery path, a sample probe tip/interface, and at least a portion of a light collection optic, such as a fiber optic. The detection module 12 preferably includes: at least a portion of the light collection optic from the sample module, a light controlling optic, and a detector. The analyzer 10 preferably includes: a data analysis algorithm and a display module. The coupling fluid delivery module 13 preferably includes: a coupling fluid reservoir and coupling fluid delivery means, such as tubing and a pump or drive system. The coupling fluid module 13 is either integrated and moves with the sample module or is connected to the sample module via a delivery tube 14.

Figure 1B:
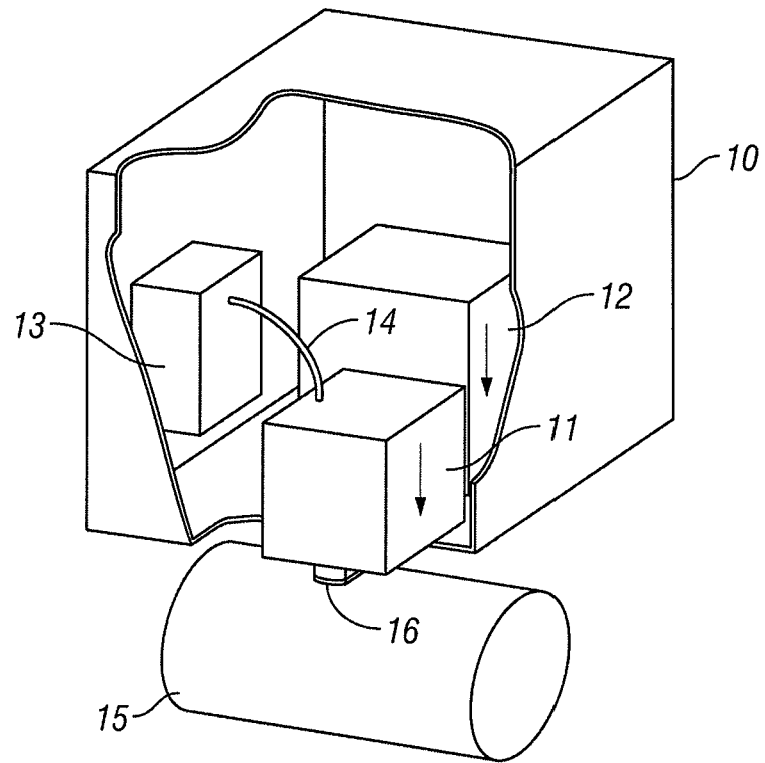

Referring now to FIGS. 1A and 1B, the analyzer couples dynamically with a sample site 15 of skin tissue. For example, as illustrated a tip of the sample probe is brought into proximate contact with a portion of a forearm. As illustrated in FIG. 1A, a sample probe tip 16 of a sample probe in the sample module, at a first point in time, located a distance away from the sample site 15. FIG. 1B illustrates the sample probe tip 16, at a second point of time, located in proximate contact with the sample site 15. Preferably, as the sample probe tip 16 is moved from a distance remote from the sample site 15 to proximate contact with the sample site 15, such as about less than 1, 2, 5, or 10 millimeters from a stationary analyzer. Preferably, the entire optic train of the analyzer is moved together or the optical train of the analyzer from a detection fiber to the detector is move together. Synchronous movement of all optical components within the optical train of the analyzer 10 and particularly within the sample module 11 and detection module 12 minimize or eliminate relative movements of optical components. Synchronous movement refers to: occurring at the same time, simultaneous movement, movement of the optics at the same rate and exactly together, where exactly is known to those skilled in the art to not account for variations due to movement from thermal effects, slippage of mechanical parts, or tolerance precision of movement of a moving mechanical system. The controlled relative orientation of all of the optical components minimizes or eliminates relative alignments of optical components. A particular example is movement of any fiber optic, such as a collection fiber optic running from the sample site through the sample module into a detection module where it is optically coupled to a detector. Any movement of the fiber optic in terms of changes in bend radius at any point along the fiber optic results in noise. Particularly, a change in the shape of a fiber optic, brought about by change in its position or radius of curvature, causes different amounts of light to be coupled between the fiber core and the fiber cladding resulting in changes in light signal levels, which results in observed spectral noise. By moving the entire optical train together, the relative orientation or movement of all parts of the fiber optic is reduced to a minimal amount or eliminated. The controlled movement of the optics results in enhanced precision of collected spectra. The collected spectra having enhanced precision then propagates through the data analysis algorithm to yield predictions of analyte values with enhanced precision and/or lower error. Optionally, the coupling fluid delivery module is integrated into components of the analyzer that move synchronously. However, preferably the coupling fluid delivery module is a separate component within the analyzer and is coupled to the sample probe tip via a delivery tube 14.

Noninvasive Glucose Concentration Determination

In a particular embodiment, light is delivered to the sample site 15 from the sample modules 11. Diffusely reflected and collected light is directed to the detection module 12 and detected as a function of wavelength. The data analysis algorithm converts the observed spectral signals into an analyte concentration of the skin/blood tissue at or about the sample site 15. For instance, the data analysis algorithm converts the observed spectra into one or more glucose concentrations representative of the body.

Coupling Fluid Delivery

Context of the coupling fluid delivery system is provided. Details of particular exemplary embodiments of movement of coupling fluid from the coupling fluid module 13 through the sample module 11, through the sample probe tip 16, and to the sample site 15 are described, infra.

Figure 2:
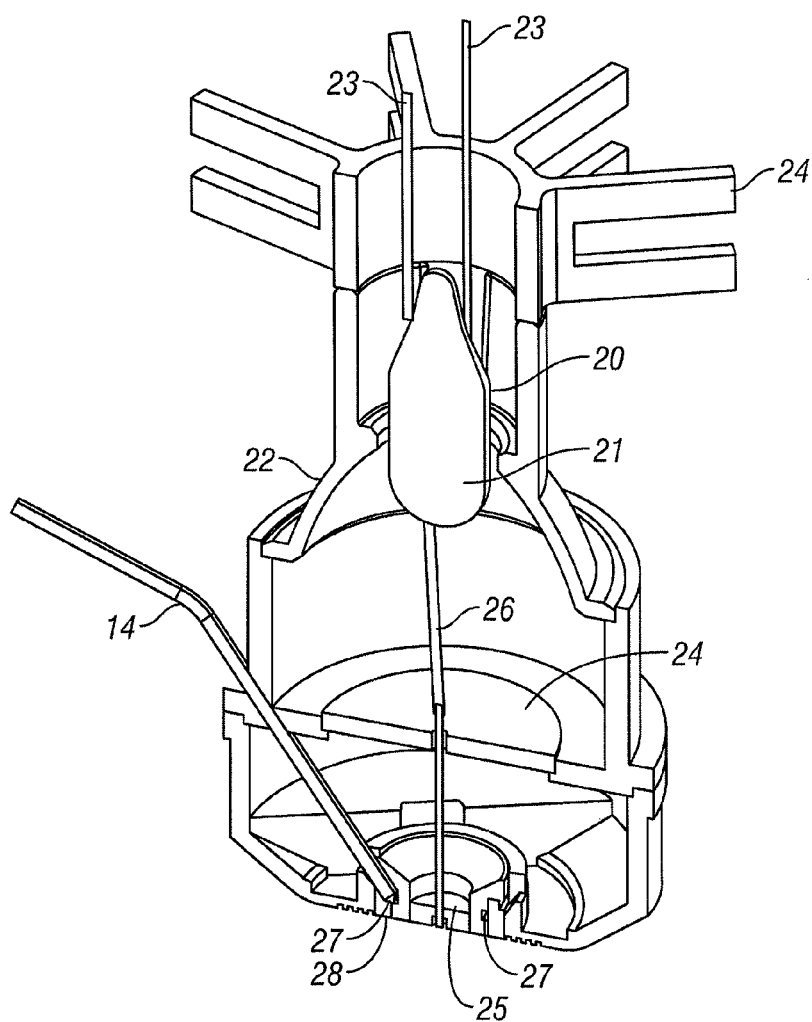
FIG. 2 illustrates an exemplary sample module.

Referring now to FIG. 2, a cross section of an exemplary sample module 11 is illustrated. This particular sample module includes: a source 20 having a filament 21, a backreflector 22, power supply lines 23, and/or a heat sink 24 having a plurality of heat dissipating fins. Light from the filament reflects off of the backreflector and travels through a first optic 24 and through a second optic 25. The first optic, preferably of silicon material, preferably absorbs at least ninety-five percent of light at wavelength in the region of about 200 to about 1100 nm and removes unwanted photonic energy from the optical path prior to the incident photons from the source penetrating into tissue at the sample site 15. The first optic 24 is not in contact with the sample site 15. The second optic 25 has a first and second surface where the second surface is part of the sample probe tip 16. During sampling, the second surface is in proximate contact with the sample site 15. The second optic preferably holds an end of a collection optic, such as a fiber optic 26. Preferably, the fiber optic penetrates at least partially through the second optic 25 and the second optic helps to mechanically hold and constrain movement of the fiber optic 26. Also illustrated is additional detail on the delivery tube 14 delivering fluid from the coupling fluid module 13. The delivery tube 14 penetrates into and optionally through the sample module to deliver fluid at or near the sample site 15, such as within about three millimeters of a center of a sample probe face. The delivery tube preferably terminates in a manifold 27 from which the coupling fluid is delivered at or near the sample site through one or more channels 28. Details of the coupling fluid delivery are provided, infra, in FIG. 3 and FIGS. 5-9.

Figure 3:
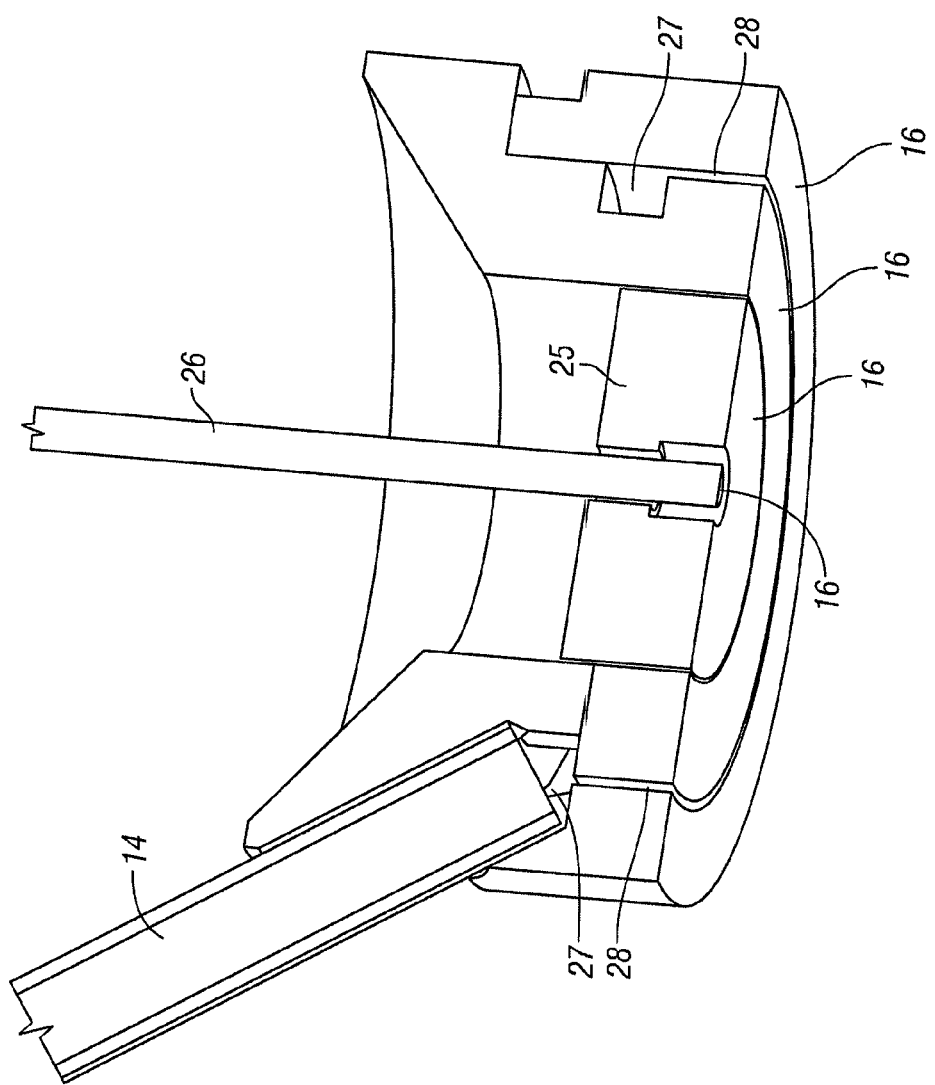
FIG. 3 illustrates and exemplary sample module probe tip.
Figure 4:
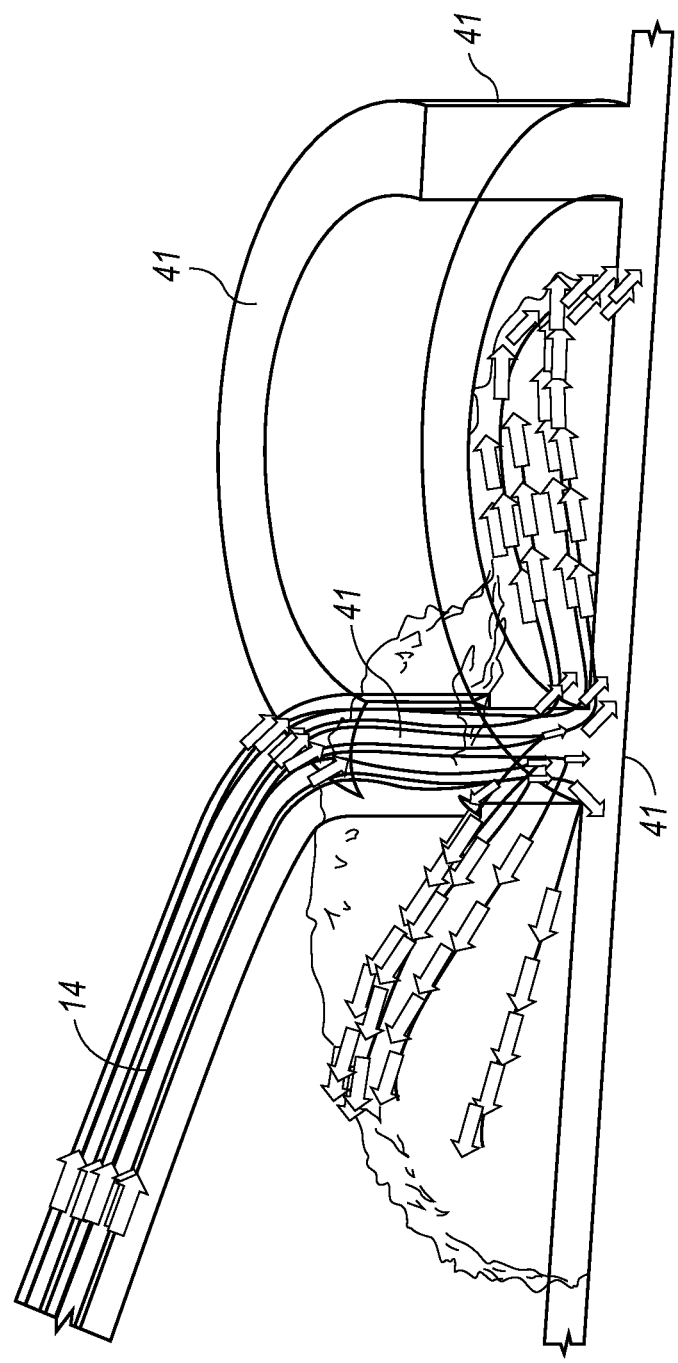
FIG. 4 illustrates a moat.
Figure 5:
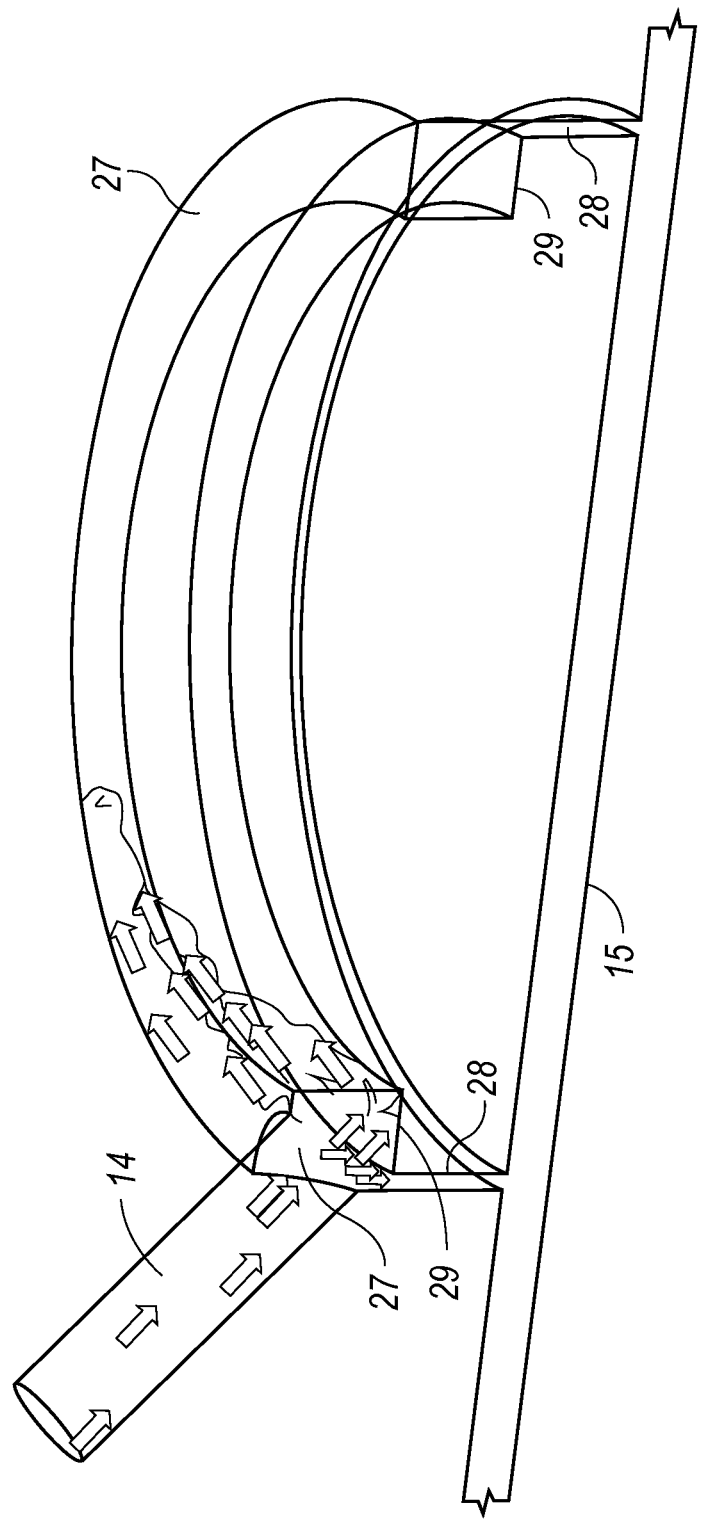
FIG. 5 illustrates a manifold/channel combination.

Referring now to FIG. 3, the sample module 11 illustrated in FIGS. 1 and 2 is expanded and re-orientated to emphasize optical elements of: the delivery tube 14, a manifold 27, and a channel 28. FIG. 3 illustrates a cross section of the tip of the delivery tube 14 terminating in a manifold 27. The manifold is used to hold a volume of coupling fluid and is used to break, or dissipate, the kinetic energy or momentum of fluid delivery from the coupling fluid module 13, as described infra. Fluid then moves from the manifold 27 to the tissue sample via a one or more channels 28. To illustrate the benefits of the manifold/channel combination, FIG. 4 illustrates an example where no manifold is used and FIG. 5 illustrates an example where a manifold is used. These two cases are described, infra.

Referring now to FIG. 4, a first embodiment of delivery of coupling fluid from the coupling fluid module 13 via a delivery tube 14 to a moat 41 is presented where fluid flows from the moat to the sample site 15. FIG. 4 is again a cross sectional view of the apparatus in proximate contact with the sample site 15. Two cases are presented. In the first case, the fluid is delivered against gravity from the bottom up to the sample site and in the second case the fluid flows with gravity down to the sample site. In the first case, where fluid is being delivered from the bottom to the moat and the tip of the sample probe is brought up to a bottom of a sample site, then the fluid completely fills the moat before it leaves the moat to wet the sample. In the second case, when the fluid is delivered in the top-down orientation illustrated in FIG. 4, the fluid does not fill the moat. Instead, the fluid flows directly from the delivery tube to the sample. While usable, this second case is not a preferred embodiment for at least two reasons. First, the momentum of the flow of the coupling fluid from the delivery tube 14 creates a fluid jet that impacts the sample site 15. The impact on the tissue at the sample site creates localized stresses and strains on the sample site, which leads to a degradation in precision of collected spectra and hence leads to decreases precision and accuracy in corresponding analyte concentration predictions arising from analysis of the collected optical spectra by the data analysis algorithm. Second, computational fluid dynamics calculations show that only part of the sample site is covered, or wetted, by the coupling fluid using a moat. Particularly, the wetted surface is nearest to the delivery tube. For ease in presentation, arrows are illustrated in the fluid to show direction of movement aligned with the orientation of the arrows and rate of flow of the fluid is indicated by the relative size and density of the arrows. The shaded fluid coverage, direction of the arrows, and magnitude of the arrows reveals that, with a top-down coupling fluid delivery system using a moat, not all of the sample site 15, which includes the area inside moat, is covered by the delivered coupling fluid. This results in collected spectra having: some spectrally reflected light, a decrease in observed spectral intensity, and decreased precision and accuracy of resulting analyte concentration predictions from the collected spectra.

Referring now to FIG. 5, an alternative embodiment of a top-down coupling fluid delivery design is presented. FIG. 5 is an expansion and reorientation of FIGS. 2 and 3. FIG. 5 is still a cross-sectional view of the apparatus in proximate contact with the sample site 15. Coupling fluid is delivered through a delivery tube 14 to a manifold 27 also referred to as a plenum. The plenum collects coupling fluid from the delivery tube 14 and then distributes the coupling fluid, as a manifold would, to the entire sample area via one or more channels 28. Stated in more detail, fluid from the delivery tube 14 hits an edge, wall, barrier, or baffle of a manifold. For example, a bottom wall 29 of the manifold 27 prevents the momentum of the delivered coupling fluid from striking tissue at the sample site 15 directly. The wall acts as a barrier that absorbs the delivery force of the coupling fluid. After striking the baffle, the coupling fluid fills or partially fills the manifold. In FIG. 5, it is observed from the shaded fluid and arrows, described infra, that after a short period of time approximately one-fourth of the manifold is filled by the coupling fluid while fluid has not penetrated down the channel 28 to the sample site.

Figure 6:
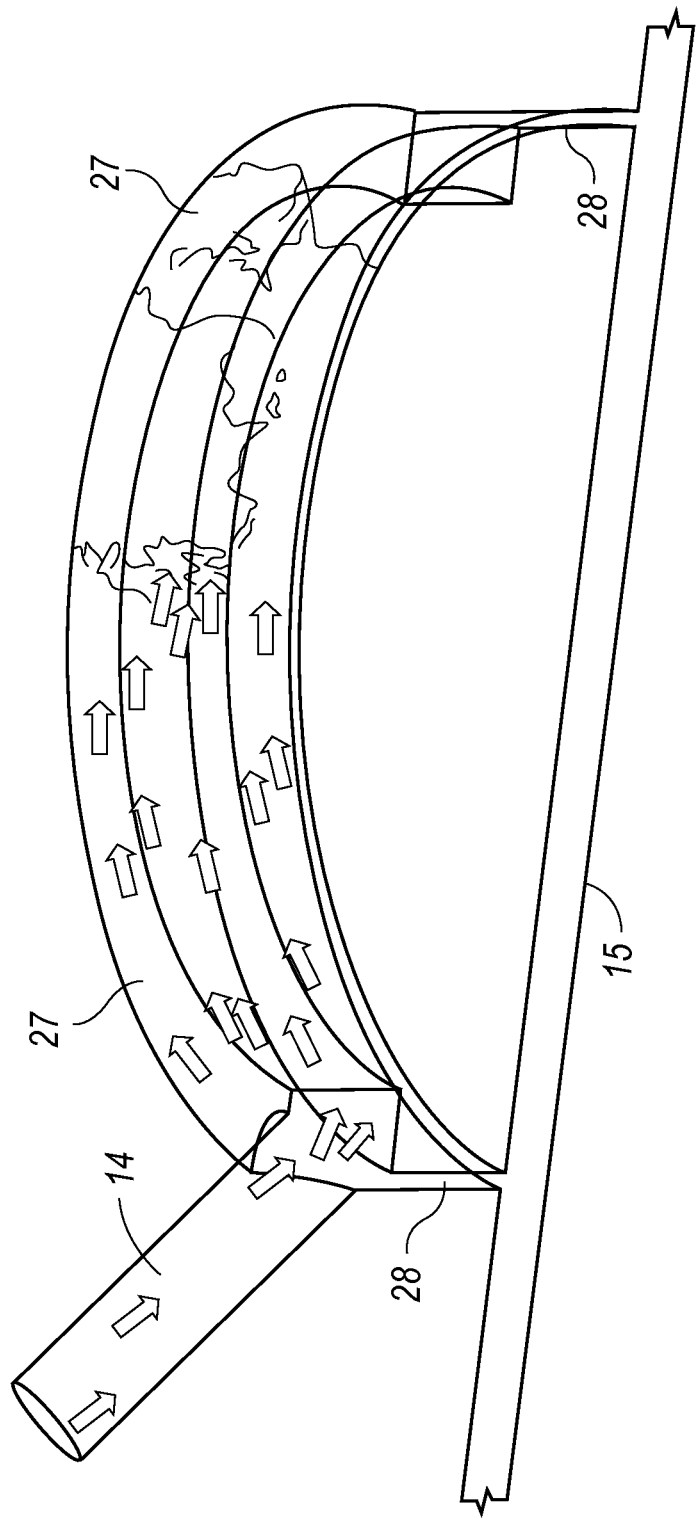
FIG. 6 illustrates coupling fluid delivery to a manifold and channel.
Figure 7:
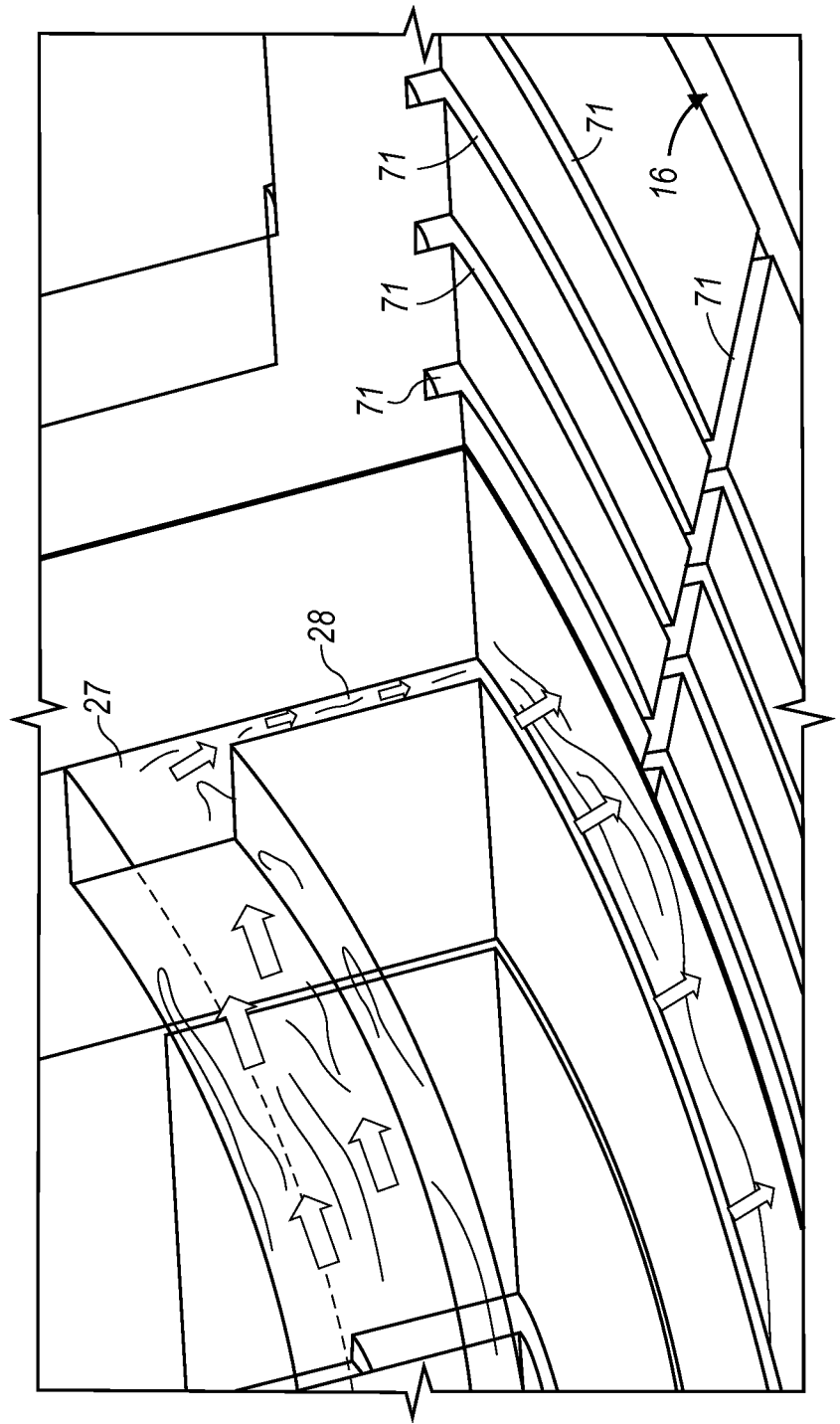
FIG. 7 illustrates coupling fluid delivery from a channel to grooves.

Referring now to FIG. 6, the apparatus of FIG. 5 is illustrated at a later time period when the coupling fluid has filled approximately eighty percent of the manifold. Computational fluid dynamics calculations, represented by the shaded coupling fluid and arrows, show that while the manifold 27 is nearly filled with coupling fluid, that the coupling fluid is only beginning to penetrate into the narrower channel 28. Thus, the manifold acts like a plenum, an open volume for fluid collection. The manifold also serves to distribute the coupling fluid circumferentially around the sample site 15 and to provide input coupling fluid to all channel inputs about the sample site 15. FIGS. 5 and 6 demonstrate that the coupling fluid partially or preferably substantially fills the manifold 27 before the coupling fluid significantly dispenses from the channel 28 to the sample site 15.

The provided example illustrates a single manifold 27 and a single channel 28 design. However, many geometries of manifolds and channels are optionally used to achieve the desired outcome of uniform coupling fluid delivery at and/or about the sample site. For example, in the provided example, a bottom wall 29 of the manifold 27 is used to force the coupling fluid to fill the manifold before the coupling fluid exits the channel. However, the coupling fluid is optionally delivered to the manifold at other angles thereby using another wall of the manifold to act as a barrier against the delivery force/momentum of the delivered coupling fluid. Similarly, baffles are optionally used in the channel to reduce flow rates in the channel relative to within the plenum. Still further, the channel illustrated in the above example is a cylinder of an annulus and is joined to the manifold all along one edge. In one alternative design, the annular channel is replaced by a series of discrete conduits, cylindrical conduits, or tubes. These tubes act the same as the annular channel in that they carry the coupling fluid from the manifold to desired locations on the sample module face as the manifold is filled. In another alternative design, the fluid is delivered from one or more sources through a dendritic distribution network, akin to that of a river delta. More generally the channel is optionally one or more lines or delivery ports that distribute fluid from one or more manifolds to one or more regions at and/or about the sample site. Ideally, the channels are uniformly filled and uniformly deliver the coupling fluid through all exits to a delivery region, such as about the sample site 15. Generally, the flow rate of the coupling fluid is faster in the plenum than in the delivery channels allowing the plenum or multiple plenums to hold an effective delivery volume fill before significant delivery of fluid through the channels to the sample site.

The relative size of the manifold 27 and channels 28 is used to affect uniform coupling fluid delivery to the sample site 15. The open, large plenum-like volume of the manifold 27 provides a region in which the coupling fluid slows down from the higher speed of the delivery tube 14. The momentum of the fluid from the delivery tube 14 is dissipated in the manifold. The fluid rapidly fills the manifold and begins to enter the narrow channel, drawn into the channel by capillary action. The fluid adheres to the solid walls of the channel more readily than it forms a surface across the channel. This is a balance of interfacial surface energy and cohesive surface energy. The cross-sectional length or width of the channel, preferably about 0.001 to 0.1 inch and more preferably about 0.003 inch or about 75 microns, is engineered to enhance the capillary action of the a particular coupling fluid, FC-40, for the metals of brass or aluminum used in the construction of the sample module. For delivery of other coupling fluids along other material, the channel geometry is appropriately adjusted.

Figure 8:
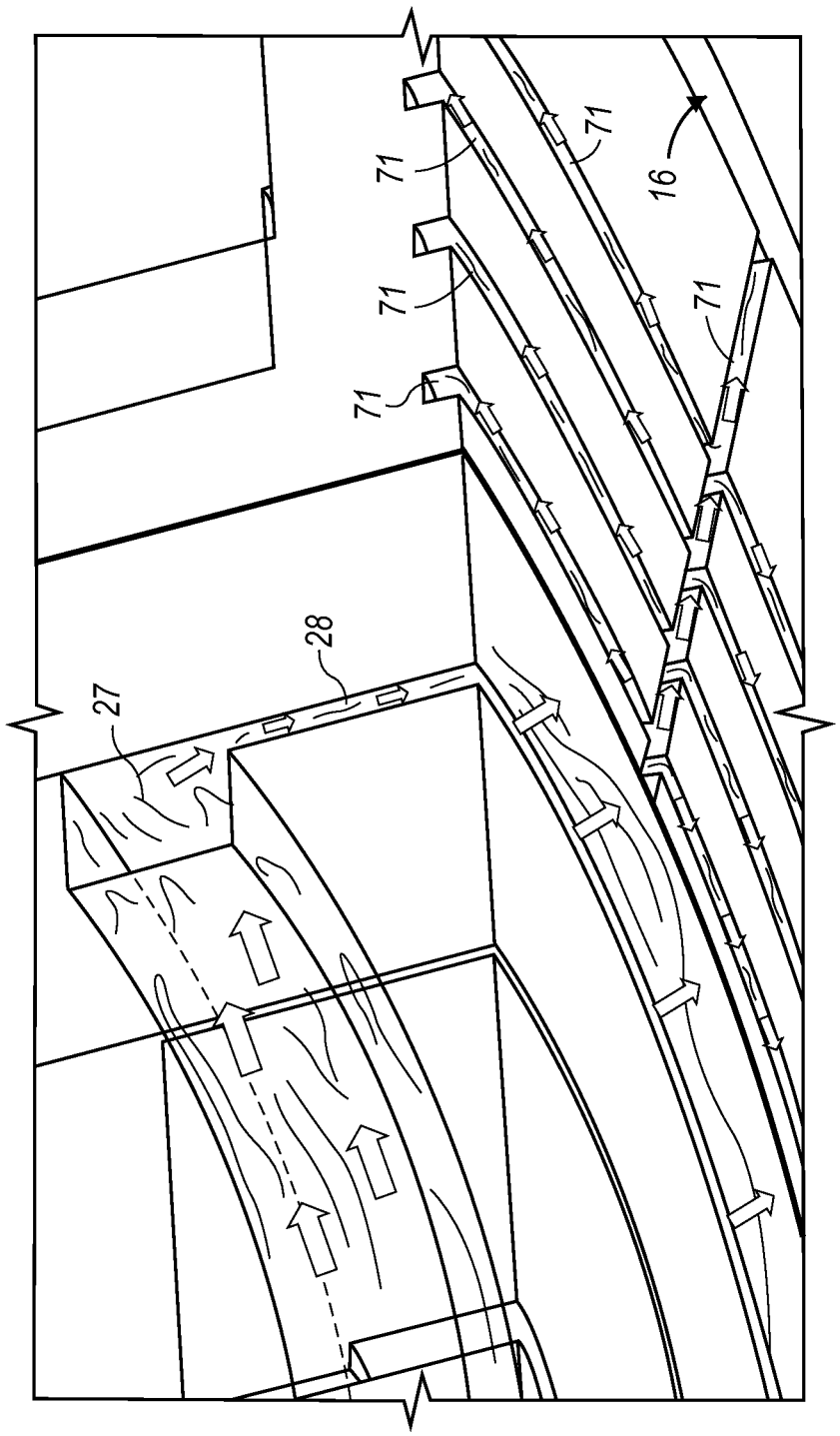
FIG. 8 illustrates distribution of coupling fluid via grooves on a sample probe tip.

Referring now to FIG. 7, FIGS. 2, 3, 5, and 6 are further expanded and re-orientated to show fluid moving from the manifold 27 through the channel 28 to a series of grooves 71. Fluid advances through the channel 28 and then along the outer surface of the sample module in all directions. When the coupling fluid reaches the grooves 71, capillary action draws the coupling fluid into and along the network of grooves 71. The capillary action rapidly draws the coupling fluid out to substantially fill one or more grooves. The dimensions and shape of the grooves are engineered to favor the capillary action. Preferably, the grooves have a cross-sectional dimension, or rectangular cross-section, of about 0.001 to 0.01 inches and more preferably about 0.004 inches or about 100 micrometers wide by about 0.001 to 0.01 inches and more preferably about 0.004 inches deep. These dimension are optimized for the coupling fluid of a fluorocarbon, such as FC-40, delivered in plastic grooves. The network of grooves is designed and located to distribute the fluid where the sample will be wetted, such as at and/or about the sample site 15. Another function of the network of grooves is to hold the fluid in these distributed locations until the sample is close enough to receive it. The capillary action, groove dimensions, and groove shapes are engineered to hold the fluid regardless of instrument orientation so that the sample probe is optionally brought to the sample site 15 from the bottom moving up, from the top moving down, or along a non-vertically aligned sample probe movement angle. FIG. 8 illustrates the progression of the coupling fluid at a later point in time from that of FIG. 7.

Figure 9:
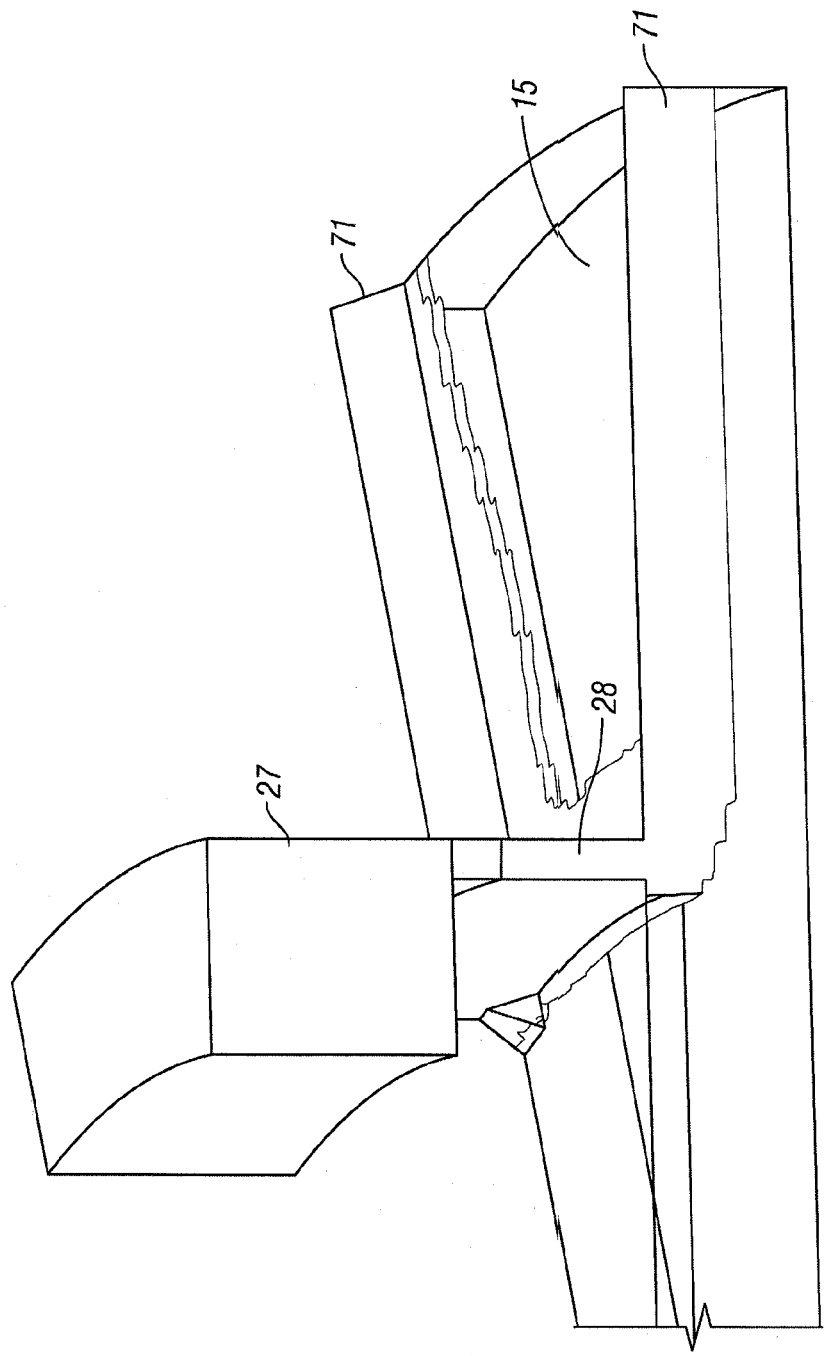
FIG. 9 illustrates coupling fluid being held in grooves.
Figure 10:
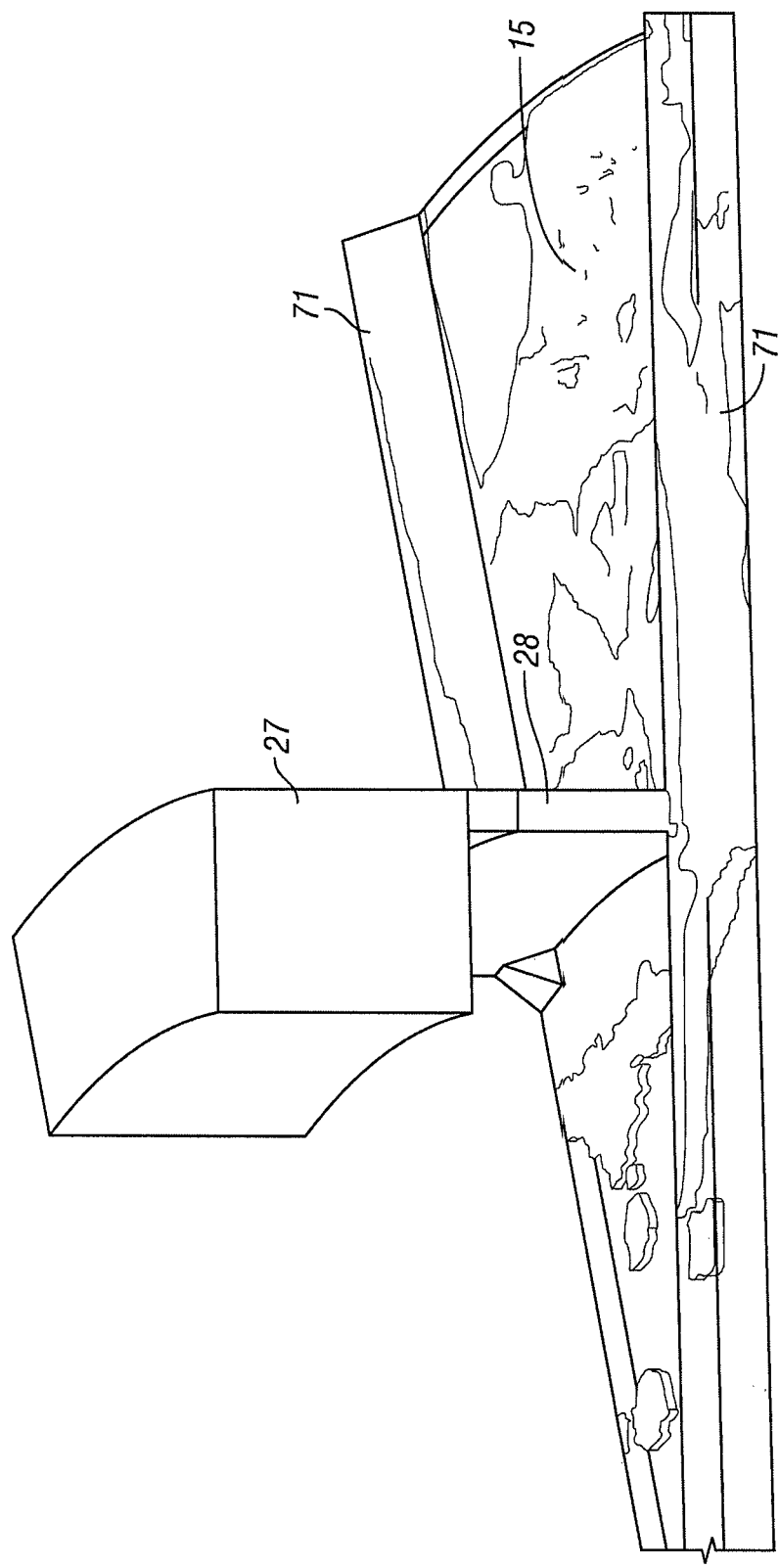
FIG. 10 illustrates coupling fluid flowing from grooves to a sample site.

Referring now to FIG. 9, FIG. 9 shows that the fluid is substantially held in the grooves, by property adhesion properties, until the sample probe tip 16 approaches the sample at the sample site 15. The inventors have determined that when the sample probe tip is about 50 micrometers (about 0.002 inches) or less from the sample, the fluid is drawn out of the grooves and onto the tissue sample by capillary action, as illustrated in FIG. 10. Thus, fluid is preferably delivered from the coupling fluid module 13 through the delivery tube 14, through the sample module 11, into the manifold 27, through the channels 28 and into the grooves 71 when the tip of the sample probe 16 is within about fifty micrometers from the tissue sample site, such as the outer layer of skin tissue. Less preferably, the coupling fluid is delivered from the coupling fluid module 13 to the sample site 15 when the tip of the sample probe 16 is within about one hundred micrometers. The inventors have determined through experiment and from computational fluid dynamic calculations that delivering the fluid when the distance between the sample probe tip 16 and the sample site 15 is about fifty micrometers or less results in substantial surface coverage of the sample site 15 by the coupling fluid. As described, supra and infra, even and total coverage of the sample site by the coupling fluid prior to optical sampling yields superior accuracy and precision of resulting analyte concentration determinations.

The inventors have determined that the optimal groove shape is rectangular with approximately the dimensions described, infra. The rectangular groove shapes hold the fluid in the grooves until the tip of the sample probe is in proximate contact about fifty microns or less from the sample site. Delivery at this close distance results in complete or nearly complete coverage of a sample site with the coupling fluid. Groove shapes, such as triangular, semi-circular, and rectangular with a larger width to depth ratio, are less preferable as they tend to leak fluid out of the grooves at larger distances between the tip of the sample probe and the sample site resulting in less complete coverage of the sample site with the coupling fluid. However, any groove shape is applicable to the invention as described herein.

Figure 11:
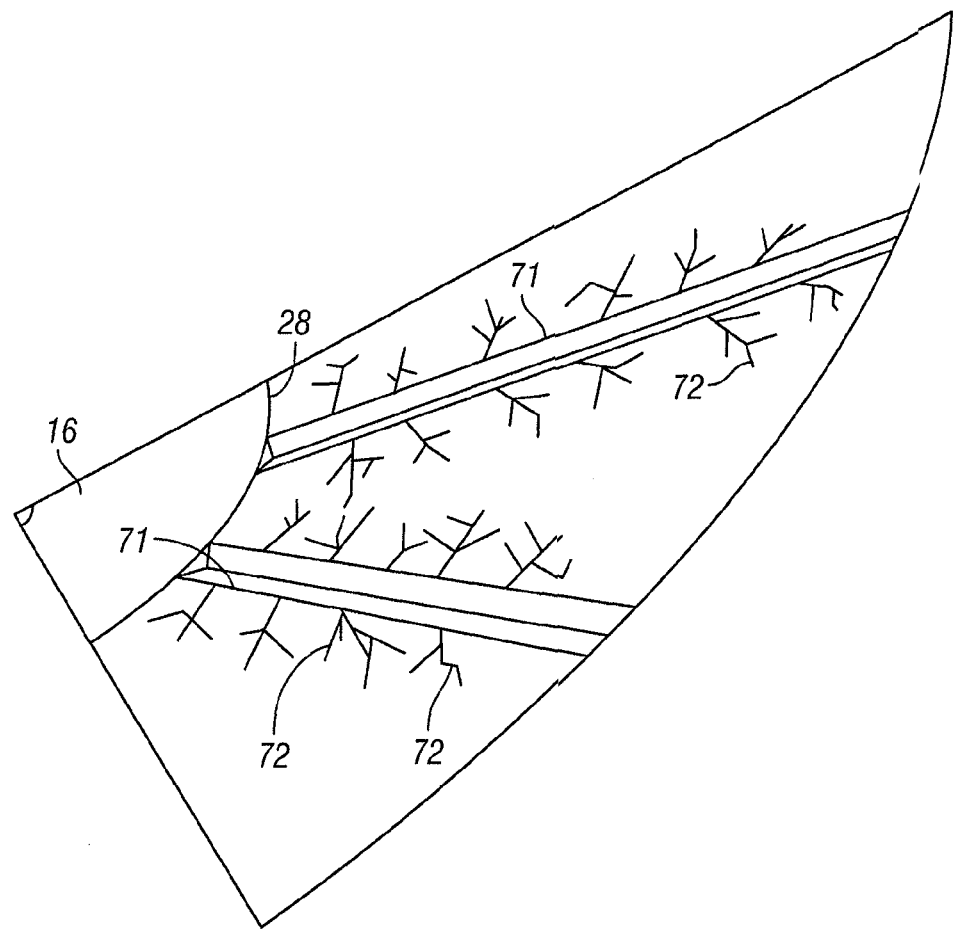
FIG. 11 illustrates grooves having induced fractures.

Referring now to FIG. 11, FIG. 9 is illustratively expanded to show optional branches emanating from the grooves. Herein, the term dendritic is used to describe the pattern formed by the multiple branches of the grooves in the sample probe face. Here, the grooves branch into multiple smaller dendritic branches that fill out the pattern on the sample probe face where the sample is to be wetted. The fluid flows from the channel to the first set of grooves, and then by capillary action, the fluid is rapidly drawn into the network of branching, dendritic channels.

As an example, the dendritic pattern of groove formation is achieved by dragging a pointed, hardened tool through a relatively brittle material. For example, an engraver tip, made from tool steel or made with a diamond tip, is driven slightly into a brittle material, such as a cured epoxy material, and dragged along the surface as if it were engraving a path in the epoxy surface. In this example, the engraved path is the groove 71. Since the epoxy material is brittle, its surface fractures forming dendritic cracks, the dendritic channels 72, emanate outwardly and/or perpendicularly from the path of the tool along the groove. The engraver tip optionally spins as it translates through the material. In contrast, if the material being engraved is soft, ductile, or malleable, the tool would leave a smooth single groove along the path. In this case, the tool plows through the surface forming a trough with raised berms on either side. Examples of materials that would yield a smooth groove are polycarbonate, acetals, and most metals. Thus, the sample probe tip preferably has grooves and optionally is manufactured with or without dendritic channels emanating from the grooves.

Parameters effecting or related to the above described invention are described, infra.

Coordinate System

Herein, an x, y, and z-coordinate system relative to a given body part is defined. An x,y,z-coordinate system is used to define the sample site, movement of objects about the sample site, changes in the sample site, and physical interactions with the sample site. The x-axis is defined along the length of a body part and the y-axis is defined across the body part. As an illustrative example using a sample site on the forearm, the x-axis runs between the elbow and the wrist and the y-axis runs across the axis of the forearm. Similarly, for a sample site on a digit of the hand, the x-axis runs between the base and tip of the digit and the y-axis runs across the digit. Together, the x,y-plane tangentially touches the skin surface, such as at a sample site. The z-axis is defined as orthogonal to the plane defined by the x- and y-axes. For example, a sample site on the forearm is defined by an x,y-plane tangential to the sample site. An object, such as a sample probe, moving along an axis perpendicular to the x,y-plane is moving along the z-axis. Rotation or tilt of an object about one or a combination of axis is further used to define the orientation of an object, such as a sample probe, relative to the sample site. Tilt refers to an off z-axis alignment of the longitudinal orientation of the sample probe where the longitudinal axis extends from the sample probe tip interfacing with a sample site to the opposite end of the sample probe. A sample probe moving perpendicular to the sample site may move along the z-axis; however, if the local geometry of the skin of the sample site is tilted, then perpendicular movement of a sample probe refers to the sample probe moving normal to the skin surface, which may be on an axis that is not the z-axis.

Tissue Stress/Strain

Preferably, a controller moves a sample targeting probe and/or a sample probe so as to make minimal and/or controlled contact with a sample tissue to control stress and/or strain on the tissue, which is often detrimental to a noninvasive analyte property estimation. Strain is the elongation of material under load. Stress is a force that produces strain on a physical body. Strain is the deformation of a physical body under the action of applied force. In order for an elongated material to have strain there must be resistance to stretching. For example, an elongated spring has strain characterized by percent elongation, such as percent increase in length.

Skin contains constituents, such as collagen, that have partially elastic spring-like properties. That is, elongation causes an increase in potential energy of the skin. Strain induced stress changes optical properties of skin, such as absorbance and scattering. Therefore, it is not desirable to make optical spectroscopy measurements on skin with varying stress states. Stressed skin also causes fluid movements that are not reversible on a short timescale. The most precise and repeatable optical measurements are therefore conducted on skin in the natural strain state, such as minimally or non-stretched stretched skin. Skin is stretched or elongated by applying loads to skin along any of the x-, y-, and z-axes. Controlled contact reduces stress and strain on the sample. Reducing stress and strain on the sample results in more precise sampling and more accurate and precise glucose concentration determinations.

Effect of Displacement on Tissue Spectra

The displacement of a tissue sample by a sample probe results in compression of the sample site. The displacement results in a number of changes including at least one of:
- a change in the localized water concentration as fluid is displaced;
- a change in the localized concentration of chemicals that are not displaced such as collagen; and
- a correlated change in the localized scattering concentration.

In addition, physical features of the sample site are changed. These changes include at least one of:
- compression of the epidermal ridge;
- compression of the dermal papilla;
- compression of blood capillaries;
- deformation of a skin layer;
- deformation of skin collagen; and
- relative movement of components embedded in skin.

Chemical and physical changes are observed with displacement of the sample probe into the tissue sample. The displacement of tissue is observed in spectra over a wide range of wavelengths from about 1100 to 1930 nm. The displacement of tissue also effects a number of additional skin chemical, physical, and structural features as observed optically.

An example of using light to measure a physical property, such as contact, stress, and/or strain, in tissue is provided.

Incident photons are directed at a sample and a portion of the photons returning from the sample are collected and detected. The detected photons are detected at various times, such as when no stress is applied to the tissue and when stress is applied to the tissue. For instance, measurements are made when a sample probe is not yet in contact with the tissue and at various times when the sample probe is in contact with the tissue, such as immediately upon contact and/or with varying displacement of the sample probe into the tissue. The displacement into the tissue is optionally at a controlled or variable rate. The collected light is used to determine properties. One exemplary property is establishing contact of the sample probe with the tissue. A second exemplary property is strain. The inventors determined that different frequencies of light are indicative of different forms of stress/strain. For example, in regions of high water absorbance, such as about 1450 nm, the absorbance is indicative of water movement. Additional regions, such as those about 1290 nm, are indicative of a dermal stretch. The time constant of the response for water movement versus dermal stretch is not the same. The fluid water movement occurs approximately twenty percent faster than the dermal stretch. The two time constants allow interpretation of the tissue state from the resultant signal. For instance, the interior or subsurface hydration state is inferred from the signal. For instance, a ratio of responses at high absorbance regions and low absorbance regions, such as at about 1450 and about 1290 nm, is made at one or more times during a measurement period. Changes in the ratio are indicative of hydration. Optionally, data collection routines are varied depending upon:

the determined state of the tissue; and/or
an observed tissue transient.

For example, the probing tissue displacement is varied with change in hydration or determined thickness of a skin layer, such as the dermal layer. The strain measurement is optionally made with a sample state probing system, a targeting system, or an optical measurement system. Tissue state probes describe herein are optionally used in conjunction with a dynamic probe, described infra.

A fluid, such as a coupling fluid, is preferably applied between the tip of the sample probe and the tissue sample site. It is determined that a highly viscous coupling fluid degrades the noninvasive analyte determination system. A highly viscous coupling fluid requires increased pressure from movement of a sample probe tip to a tissue sample site in order to displace the viscous coupling fluid.

For example, Fluorolube is a viscous paste that is not readily displaced. The pressure required for the tip of the sample probe to displace the Fluorolube results in tissue stress and strain that degrades the analytical quality of the noninvasive signal. Therefore, less viscous coupling fluids are required, such as FC-70 or FC-40 manufactured by 3M Corporation, (St. Paul, Minn.). The viscosity of the coupling fluid should not exceed that of FC-70 and preferably the viscosity of the coupling fluid should not exceed that of FC-40.

Coupling Medium

The interface between an optical probe and a skin surface at the tissue measurement site is potentially a significant source of sampling error. There are a number of distinct, but interrelating, sampling issues including:

induced tissue stress/strain observed in collected optical signal;
skin surface irregularity;
air gaps; and
refractive index mismatch.

Fluid use between a sample site and an interfacing sample probe surface is useful for a number of reasons. First, fluid allows for optical contact between a sample probe tip surface and a sample site with reduced pressure or displacement of the tissue by the probe tip. This results in reduced stress/strain. Second, coupling fluid aids in reduction of surface reflection due to optical aberrations in surface coupling and stretching of the surface tissue due to sample probe contact. Third, coupling fluid use aids in stabilizing hydration of surface tissue. Fourth, a refractive index matching coupling fluid enhances light throughput into the tissue and light collection from the tissue.

Stress/Strain

Sampling induced stress/strain is described, supra.

Skin Surface Irregularity

Skin surface irregularity results in an increase in the surface reflection of incident light. Basically, incident light normal to the surface penetrates into the skin sample based upon the difference in refractive index according to Snell's Law. For the refractive index of skin, approximately 1.38, and the refractive index of air, approximately 1.0, approximately 4% of the light will be reflected and 96% of the light will penetrate into the skin. The surface irregularities of skin mean that the incident light is not normal to the surface. This results in more reflected light, and less penetrating light.

Tissue Hydration

Air gaps near the skin surface complicate near infrared spectra interpretation. Some light penetrating into an outermost layer of skin hits an air pocket. Some light is reflected off of each surface of the air pocket. Many air pockets or poor hydration leads to a significant reduction in the percentage of incident photons that penetrate through the outermost skin layers, such as the stratum corneum, to the inner skin layer.

Refractive Index

The refractive index mismatch and Snell's Law explain part of the effects described for the skin surface irregularities and air gaps. However, the inventors have determined that a coupling fluid need not be a refractive index matching fluid, also known as an optical coupling fluid, in order to increase usable light throughput. For example, in the case of a high refractive index material, such as a lens, coming into contact with skin via a coupling fluid, the coupling fluid need not have a refractive index between that of skin and the optic in order to be beneficial. For example, the percentage of incident photons passing through a silicon lens or optic into skin is increased even with use of a coupling fluid that does not have a refractive index between that of silicon and skin. For example, a fluorocarbon, such as FC-40 manufactured by 3M Corporation, (St. Paul, Minn.) has an index of refraction of 1.290 that is not between that of skin, 1.38, and silicon, approximately 2. However, the FC-40 still increases incident photon penetration by displacement of air. Specifically, for coupling silicon and skin FC-40 is not an "index-matching medium", "optical coupling fluid", or "refractive-index matching coupling fluid"; however, it still aids in light coupling by displacing the lower refractive index air. Alternatively, a coupling fluid, such as a chlorofluorocarbon with a higher index of refraction, is called an index-matching medium. A chlorofluorocarbon with an index of refraction between that of the coupling medium and the skin will increase the number of penetrating photons due to both index of refraction matching and displacement of the air that results in a smoother surface.

Table 1 provides index of refractions for a series of chlorohydrocarbons where it is observed that as the number of chlorine atoms increases, the refractive index increases. Longer chain chlorocarbons have higher refractive indices.

Table 2 demonstrates that as the substituted halide atom increases in atomic number, the refractive index increases. Combining the information from Tables 1 and 2, it is observed that the minimum refractive index for a chlorohydrocarbon is 1.3712 and that the minimum refractive index for a non fluorohydrocarbon is 1.3712. Herein, a preferred coupling fluid comprises a fluorocarbon or a fluid with a refractive index of less than about 1.37 and preferably with a refractive index of less than about 1.32.

TABLE 1

Chlorocarbons and chlorohydrocarbons

| Molecule | Refractive Index |
|---|---|
| $CH_3Cl$ | 1.3712 |
| $CH_2Cl_2$ | 1.4244 |
| $CHCl_3$ | 1.4476 |
| $CCl_4$ | 1.4607 |

TABLE 2

Halohydrocarbons

| Molecule | Refractive Index |
|---|---|
| $CH_2Cl_2$ | 1.4244 |
| $CH_2Br_2$ | 1.5419 |
| $CH_2I_2$ | 1.7425 |

Viscosity

A fluid between a sample probe tip surface and a tissue sample beneficially has a kinematic viscosity that allows rapid movement of the fluid from between the sample probe tip and the sample site when the tip is brought into proximate contact or contact with the tissue sample. Fluorocarbons have kinematic viscosities fulfilling the requirement. In particular, FC-40 has a kinematic viscosity of 2.2 centistokes (cs). Longer chain fluorocarbons, such as FC-70 with a viscosity of 12 cs is borderline acceptable. Generally, the fluorocarbon should have a viscosity of less than about 12 cs and preferably less than about 5 cs.

Reflection

Coupling the relatively smooth surface of an optical probe with the irregular skin surface leads to air gaps between the two surfaces. The air gaps create an interface between the two surfaces that adversely affects the measurement during sampling of tissue due to refractive index considerations as described, infra. A coupling medium is used to fill these air gaps. Preferably, for an application, such as noninvasive glucose concentration estimation, the coupling fluid:

is spectrally inactive;
is non-irritating
is nontoxic;
has low viscosity for good surface coverage properties;
has poor solvent properties with respect to leaching fatty acids and oils from the skin upon repeated application; and
is thermally compatible with the measurement system.

It is possible to achieve these desirable characteristics by selecting the active components of the coupling fluid from the classes of compounds called fluorocarbons, perfluorocarbons, or those molecules containing only carbon and fluorine atoms. Nominally limiting chain length to less than 20 carbons provides for a molecule having the requisite viscosity characteristics. Generally, smaller chain lengths are less viscous and thus flow over the sample surface more readily. Longer chains are more viscous and tend to coat the sample surface with a thicker layer and run off of the sample site over a longer period of time. The molecular species contained in the perfluorocarbon coupling fluid optionally contain branched, straight chain, or a mixture of both structures. A mixture of small perfluorocarbon molecules contained in the coupling fluid as polydisperse perfluorocarbons provides the required characteristics while keeping manufacturing costs low. Additives are optionally added to the fluid.

In one embodiment, the coupling fluid is a perfluoro compound, such as those known as FC-40 and FC-70, manufactured by 3M Corporation (St. Paul, Minn.). This class of compounds is spectrally inactive in the near-infrared region, rendering them particularly well suited for sampling procedures employing near-infrared spectra. Additionally, they have the advantage of being non-toxic and non-irritating, thus they can come into direct contact with living tissue, even for extended periods of time, without posing a significant health risk to living subjects. Furthermore, perfluoro compounds of this type are hydrophobic and are poor solvents; therefore they are unlikely to absorb water or other contaminants that will adversely affect the resulting optical sample. It is preferable that the sampling fluid be formulated without the addition of other substances, such as alcohols or detergents, which may introduce artifacts into the optical sample. Finally, the exceptional stability of perfluoro compounds eliminates the environmental hazard and toxicity commonly associated with chlorofluorocarbons.

Other fluid compositions containing both perfluorocarbons and chlorofluorocarbons are also suitable as coupling fluids: for example a blend of 90% polymeric chlorotrifluoroethylene and 10% other fluorocarbons have the desired optical characteristics. Chlorotrifluoroethene is optionally used. While these compositions containing both fluorocarbons and chlorofluorocarbons have the desired optical characteristics, their toxicity profiles and their solvent characteristics render them less desirable than the previously described fluorocarbons.

Additionally, other fluid media are suitable for coupling of an optical probe to a tissue measurement site, for example, skin toner solutions or alpha hydroxy-acid solutions.

Operation

During use, a quantity of sampling fluid is placed at the interface of the tissue measurement site and the fiber optic probe so that the tissue measurement site and the fiber optic probe are coupled leaving no or minimal air spaces between the two surfaces. Several methods of delivery sequence are described, infra.

In one method of coupling the interface of a tissue measurement site and a tip of a sample probe, a small amount of coupling fluid is placed on the skin surface prior to placing the fiber optic probe in close proximity or in contact with the sample site.

Another method of coupling the interface of a tissue measurement site and a tip of a sample probe is to place coupling fluid on the tip of the sample probe and bringing the sample probe into contact with a surface proximate the skin sample site.

Yet another method of coupling a tissue measurement site to an analyzer is to spray the tissue sample site with the coupling fluid and/or to spray the tip of the sample module and/or bundle prior to bring the sample into contact or close proximity with the analyzer.

An additional method of coupling a measurement site to a tip of a sample module is to deliver the coupling fluid while the tip of the sample module is in motion. For example, coupling fluid is delivered through small tubes that terminate at the tip of the sample module near the area of photon delivery and/or near the area of photon collection. For example, a fluorocarbon is dropped onto the tissue sample site through tubes terminating next to a central collection fiber.

In still yet another method of coupling a tissue measurement site and a tip of a sample probe, channels or ridges are provided that allow excess coupling fluid to be pushed out of the way or to drain off through gravity. A primary intent of this embodiment is to prevent applying undue pressure to the sample site when the tip of the sample probe is brought into close proximity and/or contact with the sample site. Pooling of excess coupling fluid is prevented by these channels. For example, a hydraulic effect created by the sample module pressing on coupling fluid on its way to the sample site is relieved by having channels through which excess coupling fluid freely flows when pressurized.

Another method of coupling the interface between the tissue measurement site and the tip of a sample probe is to first bring the tip of the sample probe into contact with the sample site, remove the sample probe from the sample site, deliver the coupling fluid, and then again bring the sample probe into close proximity with the sample site. This method eases locating the skin when a movable sample probe is used as described in U.S. patent application Ser. No. 11/117,104, filed Apr. 27, 2005, which is incorporated herein in its entirety by this reference thereto. In addition, the elapsed period of time between coupling fluid delivery and optical sampling, also known as the measurement, is minimized thus reducing the risk of evaporation of the coupling fluid prior to sampling.

Still another method is to pull a partial vacuum on or about a tissue sample site. For example, the tip of an optical probe is pulled away from the sample site after making contact. In a second example, the tip of tubing filled with a coupling fluid is in contact with a sample site and fluid is withdrawn from the tubing or is backed off from the tip of the tubing. This movement of the coupling fluid creates a partial vacuum. Creating a partial vacuum creates a small convex tissue meniscus. Fluid, such as interstitial fluid, flows into the meniscus. This results in increased concentration of the analytical target of interest in the sampled optical tissue. Alternatively, applying a small negative pressure reduces a negative meniscus making the sample more readily sampled with a flat optical surface.

Yet another method of applying coupling fluid to a tissue site is to warm the coupling fluid to a target temperature prior to application. Examples of target temperatures include about 88, 90, 92, 94, 96, and 98 degrees Fahrenheit. Optionally, the tip of the sample probe and/or surface of the sample site are adjusted to or toward this first target temperature or to their own target temperature. Preferably, the two target temperatures are the same in order to reduce sampling variations resulting from temperature variation. A variation is to independently control or not control the sample site, coupling optic, and coupling fluid temperature.

Still yet another method of applying coupling fluid includes a step of removing coupling fluid from the sample site. Methods of removal include: waiting for a period of time to allow evaporation, allowing gravity induced run off of the fluid, and/or wiping off with a material, such as an absorbent cloth or wipe.

An additional method of providing a coupling fluid between a tissue site and an optical probe is to apply coupling fluid multiple times. For example, about one to ten microliters of coupling fluid is applied two or more times, preferably with the coupling fluid being delivered through the sample probe contacting face.

Optionally, coupling fluid is used to clean a sample site. For example, coupling fluid is applied to the sample site and removed as above in order to remove sample debris.

Yet another method of providing coupling fluid between a tip or an end of a sample probe and a tissue site or sample site is to determine contact of a z-axis movable sample probe tip from a response signal, such as a pressure sensor or a force pressure sensor, a response from a broadband source, or from a response to a photons emitted from a light emitting diode. For example, a light emitting diode is optionally used outside of the range detected by detectors coupled to a broadband source element in a sample module. For instance, the light emitting diode wavelength is centered at a spectral feature, such as due to water, fat, or protein, or within an optical window such as in the 'H', 'J', or 'K' band regions of the electromagnetic spectrum. An additional detector element is optically associated with the light emitting diode. For instance, a broadband source is used in conjunction with a grating from about 1100 to 1800 nm. A light emitting diode and its associated detector are used outside of the detected broadband source region to detect, through intensity change, contact of a sample probe, analyzer, or sample probe tip with a tissue sample. Particular water absorbance features that are optionally used occur at about 1900, 2000, or 2500 nm.

In still yet another embodiment of the invention, fluid is delivered from a reservoir to a manifold where the fluid is delivered to a channel. From the channel, the fluid enters one or more grooves that optionally have fractures.

Furthermore, certain non-fluid media having the requisite optical characteristic of being near-infrared neutral are also suitable as a coupling medium, for example, a GORE-TEX membrane interposed between the probe and the surface of the measurement site, particularly when used in conjunction with one of the fluid media previously described.

Localized Delivery

Preferably, coupling fluid covers the entire sample site prior to sampling. Volume requirements for the various modes of delivery for a sample are small, such as less than about fifty microliters. Preferably about five to thirty microliters of coupling fluid are applied to the sample site. For a sample site of about two to six millimeters in diameter, eight plus or minus one to two microliters is typically sufficient. Precision and/or accuracy of volume of delivery is important in order to avoid excess waste, sufficient coverage, and/or undue pooling. Excess fluid results in optically observed stress/strain, which degrades analyte measurement, when the fluid is displaced by bringing a sample probe head into contact with a sample site through displacement of the fluid. The target volume of delivery is dependent upon the sample probe geometry and size.

In one embodiment, a driving force is applied to a fluid, such as a coupling fluid or optionally an optical coupling fluid. The driving force delivers the fluid delivers fluid at and/or near the sample site. As described herein, a number of driving force methods of delivery exist including: via spraying, dribbling, misting, through a gravity feed system, via capillary action, via a peristaltic pump, or driven by a motor or a piston. Preferably, the fluid is delivered at the sample site in a controlled manner.

Microfluidic Channel

Preferably, one or more microfluidic channels or lumens are localized about a central optic in a sample probe or sample probe face. The microfluidic channel is a tube or tubular opening, canal, duct, or cavity. The lumens or microfluidic channels are optionally of any geometric shape, such as a circle, oval, triangle, square, or other polygonal shape. The lumens are either in contact with the central optic, are embedded in a coating material, or are located in close proximity to the coating material. Preferably, the lumens are extruded or co-extruded for ease of manufacture. An example of a central optic is a core, cladding, and optional buffer of a fiber optic. The microfluidic channel allows passage of a fluid through the sample probe tip to the sample site. Preferably, the fluid is delivered at a multitude of sites circumferentially distributed about a central sample site area, such as about a central collection fiber optic. Circumferential delivery of fluid enhances surface coverage of the sample site by the fluid. For example, a dense fluid, such as a fluorocarbon, travels with gravity. On a slanted surface, such as a skin sample site, delivery of the fluorocarbon on only one side of the sample site results in poor or no coverage of the sample site when gravity pulls the fluid downhill away from the sample site. Delivery of the fluid at multiple points around the sample site allows coverage of the sample site for any non-level orientation of the sample site. The number of lumens in this example is optionally one or more. For example, two, four, or six lumens are used to deliver a coupling fluid to the sample site. The use of a larger number of lumens helps to insure coverage of the sample site by the coupling fluid.

Fluid Delivery Channel

Channels are used as a low resistance flow conduit for a fluid, such as a coupling fluid. The channels enhance delivery of the fluid across the sample probe tip about a sample interface sampling site. The fluid readily travels through one or more channels about the sample probe surface. The channels provide a pathway for rapid delivery of the fluid with minimal applied pressure from the fluid movement being delivered to the skin surface. Capillary action then distributes the fluid from the channel to the remaining surface of the sample probe tip to substantially cover the optically sampled region.

There exist a number of benefits of a channel. A channel scavenges excess fluid during the measurement process. Extra fluid on the sample site has at least two negative impacts. First, too much fluid on the sample site allows incident light to reflect between the skin and the sample probe head surface to a detection optic resulting in light, having properties not unlike specularly reflected light, that has not entered into the skin sample site with corresponding interaction with the analyte of interest. This light degrades analyte measurement. Second, excess fluid on the sample site is displaced as the sample probe surface is brought into proximate contact with the sample site. Since fluid has a resistance, the displacement of the fluid results in stress/strain on the sample site. Thus, a channel for removal of excess fluid results in a higher signal due to a higher percentage of detected photons having interacted with the analyte of interest and a reduced noise due to the reduction of stress/strain induced spectral signals. A channel is filled or partially filled actively, such as with a pump, or passively, such as through a gravity flow.

A channel is optionally filled or partially filled with a fluid through:
  an internal hole after contact of the sample probe head with the skin,
  through application of fluid to the sample probe head surface with subsequent contact with skin;
  through application of fluid to the sample site with subsequent contact with the sample probe head;
  from capillary action of fluid after the sample probe head is already in contact with the sample site; or
  any combination of the above.

Radial Channel

Radial distribution of coupling fluid via channels has several benefits. First, the radial distribution of channels enhances fluid delivery over and around the optically sampled skin tissue. Second, the distance of required capillary action of the fluid between the sample probe tip and the sample site is minimized. This enhances complete coverage of the sample site with the fluid and minimizes time requirements for capillary action coverage of the sample site. Third, one or more of the radially extending channels allow an escape path for excess fluid. The escape path reduces optically observed stress/strain tissue site stress strain as reduced pressure is applied to the sample site when:
  fluid is forced through a delivery hole, excess pressure of fluid delivery is relieved through the escape channel; and/or
  force is applied to the fluid as a result of bringing into proximate contact the sample probe head surface and the skin sample site, excess pressure is relieved through the escape channel.

In yet another embodiment of the invention, a sample probe head includes a combination of channel types. Preferably, the axis of extending channels is along a long axis of the sample site body part, such as along an x-axis substantially defined by an elbow and wrist of an arm. The gently sloping skin along an x-axis of an arm will inherently stay in contact longer with the channel as opposed to the curved shape of the arm along a y-axis across the arm. The combination of channel types allows:
  distribution of fluid about a sample site;
  a pressure relief channel; and
  flow of fluid between interconnecting channels.

Generally, any number of channels and any geometric shape or distribution of channels on the sample probe head may be used depending upon the specific fluid distribution patterns and/or timing of fluid delivery requirements.

In yet another example, fluid is delivered to the sample site when there exists a thin spatial air gap between the sample probe tip surface and the sample site. For instance, a fluid is delivered in close proximity to a collection optic. The fluid contacting both the sample probe tip surface and skin will radiate outward as a result of capillary action. The radial movement of the fluid results in a negative pressure relative to standard atmospheric pressure. The negative pressure pulls the skin into proximate contact with the sample probe tip surface through a thin layer of the fluid. The minimal change in pressure delivers enough negative force to the skin to pull the skin into contact with the sample probe tip in an elastic process. The elastic nature of the force results in replicate measurement lacking an optically observed historesis effect due to being in a linear range of the visco-elastic tissue response. For example, fluid is delivered when a distance between the sample probe head surface and skin surface is:
  less than a drop diameter size of the fluid,
  at a distance of less than about 0.25 mm;
  at a distance of less than about 0.15 mm; and/or
  at a distance that creates an effective diameter, such that the resultant negative pressure is sufficient to draw into proximate contact the sample probe head surface and skin surface.

Hence, a method of fluid delivery is presented where the step of fluid delivery itself to the gap between a sample probe tip surface and skin sample site results in movement of the skin into proximate contact with the probe tip.

Automated Delivery

An automated coupling fluid delivery system is used to deliver coupling fluid to a sample site with minimal human interaction. An automated coupling fluid delivery system provides many benefits including:
  accurate fluid delivery volume;
  precise fluid delivery volume;

accurate fluid delivery location;
precise fluid delivery location;
software controlled delivery;
delivery with minimal user input; and/or
ease of use.

Delivery of coupling fluid to a sample site is preferably performed by a lay user in a convenient manner. Automated control of one or more of the delivery steps is therefore preferential as the task is simplified for the user and controls to the delivery are established by the apparatus.

For example, fluid is delivered from a reservoir to a sample site via delivery means. The fluid is forced through the delivery path via driving means. Examples of these elements are provided, infra.

Reservoir

A reservoir or container of coupling fluid is maintained so that a supply of coupling fluid is available for use with sampling. Maintaining a reservoir with the analyzer or having a reservoir integrated into the analyzer reduces the number of items that are independently handled by a user. This reduces the complexity of a noninvasive measurement and results in overall better performance in terms of accuracy and precision. Examples of reservoirs or containers include containers of various sizes, a syringe, a cartridge, a single use packet, a blister pack, a multiuse container, or a large auxiliary container. The reservoir is optionally a disposable or reusable. For instance, a small refillable reservoir is maintained within a sample module or within an analyzer. This allows, for example, the analyzer to be portable. In another instance, an external reservoir is coupled to the analyzer in either a permanent or removable fashion. Larger reservoirs are useful due to less frequent refilling requirements. Smaller reservoirs, such as a reservoir of less than one or two milliliters are still useful for multiple measurements as a preferred coupling fluid delivery volume is less than fifty microliters per use.

Delivery Means

Coupling fluid is moved from the reservoir to a sample site through delivery means, such as tubing, flexible tubing, or channels. The delivery means optionally include a gate or a variable resistance flow section, especially when the housed reservoir is in close proximity to the sampling site. The coupling fluid is optionally routed through or integrated into a sample probe module. Optional routing through the sample module allows for delivery within close proximity to the sample site, such as within one inch. Delivery in an accurate area about a sample results in adequate coverage of the sample site while requiring less coupling fluid volume. For example, delivery near the sample site center allows about 5, 8, 10, 20, 30, or 40 microliters of coupling fluid to adequately cover the sample site. In addition, routing through the sample module allows movement of the sample module by a user to also control routing of the integrated delivery means without an additional action. In addition, the dual movement maintains tight control of the coupling fluid delivery to the sample site in terms or precision and accuracy of position of delivery. Precision and accuracy is further enhanced by the use of a guide coupling the sample module to the sample site. In an additional embodiment, the delivery channels or tubes run by thermal control means, such as a heat element, described infra. In still yet another embodiment, the delivery means are thermally insulated.

Driving Means

Means are used to deliver coupling fluid to a sample site. Driving means are available in a number of forms, such as via a motor, a solenoid, a gear, a piston, a peristaltic pump, gravity feed, capillary action, or a magnetic drive. Power supplying the driving means include potential energy, electrical sources, manual force, gravity, and magnetic fields. Driving means optionally push or pull the fluid. Further, driving means are optionally connected to the reservoir or to the delivery means.

Combinations and permutations of the coupling fluid delivery methods described herein are also usable without diverting from the scope of the invention.

While the invention is described in terms of noninvasive glucose concentration estimation, the methods and apparatus described herein also apply to estimation of additional blood tissue analytes.

Those skilled in the art will recognize that the present invention may be manifested in a variety of forms other than the specific embodiments described and contemplated herein. Departures in form and detail may be made without departing from the spirit and scope of the present invention. Accordingly, the invention should only be limited by the Claims included below.

The invention claimed is:

1. A sample probe configured to communicate with a noninvasive spectroscopic analyzer to determine an analyte property from a sample site of a body part, said sample probe comprising:

a sample probe tip and a manifold within said sample probe terminating proximate said sample probe tip, said manifold configured to receive a coupling fluid from a fluid reservoir and comprising at least one fluid redirecting surface, said at least one fluid redirecting surface configured to dissipate kinetic energy of the coupling fluid as the coupling fluid is received from said fluid reservoir; and said sample probe tip comprising a first optic and at least one channel extending from said manifold and to a surface of said sample probe tip, said at least one channel configured to distribute the coupling fluid from said manifold to the surface of said sample probe tip, the surface of said sample probe tip forming a pathway for dispersion of the coupling fluid.

2. The sample probe of claim 1, wherein said manifold is configured so that the coupling fluid moves at a greater flow rate in said manifold than in said at least one channel.

3. The sample probe of claim 1, wherein said manifold is configured to at least partially fill with the coupling fluid.

4. The sample probe of claim 1, wherein said at least one channel is configured to circumferentially distribute the coupling fluid about a center of said sample probe tip.

5. The sample probe of claim 1, wherein said at least one channel comprises a cross-sectional dimension of less than five thousandths of an inch and is configured so that the coupling fluid flows by capillary action from said manifold into said at least one channel.

6. The sample probe of claim 5, further comprising at least one groove in the surface of said sample probe tip forming part of the pathway for dispersion of the coupling fluid, wherein said at least one groove comprises a cross-sectional dimension of less than 0.01 inch.

7. The sample probe of claim 1, further comprising at least one groove in the surface of said sample probe tip forming part of the pathway for dispersion of the coupling fluid, wherein said at least one groove is configured so that the coupling fluid flows by capillary action into said at least one groove.

8. The sample probe of claim 1, wherein said sample probe tip is configured so that the coupling fluid moves to a delivery site within three millimeters of a center of said sample probe tip.

9. The sample probe of claim 1, in combination with said non-invasive spectroscopic analyzer, wherein said sample probe tip is configured to move less than five millimeters relative to said non-invasive spectroscopic analyzer to make proximate contact with a sample site during a measurement.

10. The sample probe of claim 9, further comprising an optical train connecting a tip of a collection fiber at said sample probe tip to a detector, wherein said optical train is configured to move in unison with said sample probe tip when said sample probe tip moves relative to said non-invasive spectroscopic analyzer.

11. The sample probe of claim 1, further comprising a second optic configured to absorb greater than ninety-five percent of light in a wavelength range of 200 nm to 1100 nm entering from a source in said sample probe,
wherein said first optic is configured to mechanically hold a tip of at least one collection fiber.

12. The sample probe of claim 1, wherein the coupling fluid comprises a refractive index of less than 1.32 and a viscosity of less than twelve centistokes.

13. The sample probe of claim 1, wherein said manifold extends parallel to the surface of said sample probe tip.

14. The sample probe of claim 1, further comprising a force pressure sensor configured to determine a contact between said sample probe tip and a sample site.

15. The sample probe of claim 1, wherein said manifold is configured to at least partially fill with the coupling fluid before the coupling fluid distributes from said at least one channel to the surface of said sample probe tip.

16. The sample probe of claim 1, wherein said manifold comprises an annular channel extending around a center of said sample probe tip, said annular channel configured to circumferentially distribute the coupling fluid about the center of said sample probe tip.

17. The sample probe of claim 1, wherein said at least one channel is configured to reduce a flow rate of the coupling fluid.

18. The sample probe of claim 7, wherein said at least one groove comprises dendritic pathways.

19. A method of delivering a coupling fluid to a sample site of a body part, the method comprising:
delivering a coupling fluid from a fluid reservoir to a manifold within a sample probe, said manifold terminating proximate a sample probe tip of said sample probe and comprising at least one fluid redirecting surface, said at least one fluid redirecting surface configured to dissipate kinetic energy of the coupling fluid as the coupling fluid is received from said fluid reservoir; and
delivering the coupling fluid from said manifold to a surface of said sample probe tip through at least one channel of said sample probe tip running transversely from said manifold and to the surface of said sample probe tip, the surface of said sample probe tip forming a pathway for dispersion of the coupling fluid, said sample probe tip comprising an optic,
wherein said sample probe is configured to communicate with a non-invasive spectroscopic analyzer to determine an analyte property from a sample site.

20. The method of claim 19, further comprising moving the coupling fluid in said manifold at a greater flow rate than in said at least one channel.

21. The method of claim 19, further comprising at least partially filling said manifold with the coupling fluid.

22. The method of claim 19, further comprising at least partially filling said manifold with the coupling fluid before distributing the coupling fluid from said at least one channel to the surface of said sample probe tip, wherein said delivering the coupling fluid through said at least one channel comprises delivering the coupling fluid through said at least one channel by capillary action.

23. The method of claim 19, further comprising circumferentially distributing the coupling fluid about a center of said sample probe tip using said at least one channel.

24. The method of claim 19, wherein the surface of said sample probe tip comprises at least one groove forming part of the pathway for dispersion of the coupling fluid, and further comprising moving the coupling fluid by capillary action into said at least one groove.

25. The method of claim 19, further comprising determining a contact between said sample probe tip and a sample site using a force pressure sensor.

26. The method of claim 19, wherein said manifold comprises an annular channel extending around a center of said sample probe tip, said annular channel configured to circumferentially distribute the coupling fluid about the center of said sample probe tip.

27. The method of claim 19, wherein said at least one channel is configured to reduce a flow rate of the coupling fluid.

28. The method of claim 19, further comprising delivering the coupling fluid from said sample probe tip to a delivery site within three millimeters of a center of said sample probe tip.

* * * * *

UNITED STATES PATENT AND TRADEMARK OFFICE
CERTIFICATE OF CORRECTION

| | | |
|---|---|---|
| PATENT NO. | : 8,718,738 B2 | Page 1 of 1 |
| APPLICATION NO. | : 12/393867 | |
| DATED | : May 6, 2014 | |
| INVENTOR(S) | : Blank et al. | |

It is certified that error appears in the above-identified patent and that said Letters Patent is hereby corrected as shown below:

On the Title Page

Page 1 (item 63, Related U.S. Application Data) at line 2, Change "which is" to --and--.

Signed and Sealed this
Twenty-third Day of June, 2015

Michelle K. Lee
*Director of the United States Patent and Trademark Office*